United States Patent [19]

Pressly, Sr. et al.

[11] Patent Number: 5,613,952
[45] Date of Patent: Mar. 25, 1997

[54] SAFETY SYRINGE

[75] Inventors: William B. S. Pressly, Sr., Greer, S.C.;
Charles A. Vaughn, Sr., Duluth, Ga.;
G. Samuel Brockway; Thomas R. Ellis, both of Lawrenceville, Ga.

[73] Assignee: Syringe Develpoment Partners, Lawrenceville, Ga.

[21] Appl. No.: 481,093

[22] Filed: Jun. 7, 1995

Related U.S. Application Data

[63] Continuation-in-part of Ser. No. 359,001, Dec. 16, 1994, abandoned, which is a continuation of Ser. No. 813,115, Dec. 23, 1991, Pat. No. 5,211,629.

[51] Int. Cl.$^6$ ........................................ A61M 5/00
[52] U.S. Cl. .......................... 604/110; 604/195; 604/111
[58] Field of Search ................................ 604/110, 195, 604/192, 187, 263, 198, 207, 218, 111, 222

[56] References Cited

U.S. PATENT DOCUMENTS

| | | | |
|---|---|---|---|
| 2,460,039 | 1/1949 | Scherer et al. | |
| 3,941,129 | 3/1976 | Pleznac | 604/207 X |
| 4,838,869 | 6/1989 | Allard | |
| 4,921,486 | 5/1990 | DeChellis et al. | |
| 4,973,316 | 11/1990 | Dysarz | |
| 4,994,034 | 2/1991 | Botich et al. | |
| 4,997,423 | 3/1991 | Okuda et al. | 604/218 X |
| 5,114,410 | 5/1992 | Batlle | |
| 5,211,629 | 5/1993 | Pressly et al. | 604/110 |
| 5,242,405 | 9/1993 | Howe | 604/218 X |

FOREIGN PATENT DOCUMENTS

| | | |
|---|---|---|
| 2197792 | 6/1988 | United Kingdom |
| 90/03196 | 9/1988 | WIPO |
| 90/06146 | 12/1989 | WIPO |

*Primary Examiner*—John D. Yasko
*Attorney, Agent, or Firm*—Hardaway Law Firm, P.A.

[57] ABSTRACT

A syringe apparatus and process for using the same is provided, the syringe apparatus having a barrel, a plunger movable within the barrel, a needle assembly attached to an end of the barrel and having a passageway therethrough, a deformable base positioned within the barrel, flexible supports included on the deformable base, a spring within the passageway of the needle assembly, a hollow needle passing through the passageway, an enlarged head on the needle, and a rupturable web on an end of the plunger, whereby when the plunger moves through the barrel toward the needle assembly, a fluid can be moved from the barrel through the hollow of the needle, and continued movement of the plunger flexes the supports and moves the deformable base downwardly until such time a sufficient force is imparted to the rupturable web by the enlarged head to tear the web, the deformable base then releasing the needle due to force applied by the spring to project the needle into the interior of the plunger. Seals are provided for making a liquid impervious seal on both ends of the syringe after the needle is retracted. The seal on the end left open by needle retraction is a closing member which can be used to seal off the opening without placing a user's hands in front of the opening. The syringe includes indicia that is revealed upon needle retraction to label the syringe as a biohazard. A syringe apparatus using a deformable base, enlarged needle head and needle assembly of an alternative embodiment is also provided wherein sacrificial supports in the needle assembly are utilized and severed by the deformable base.

40 Claims, 17 Drawing Sheets

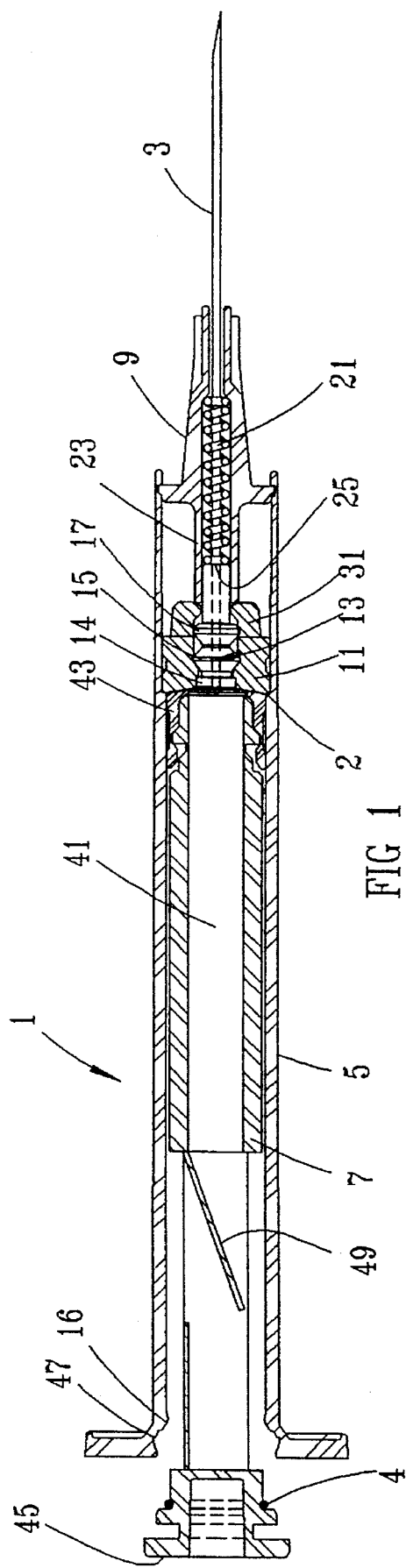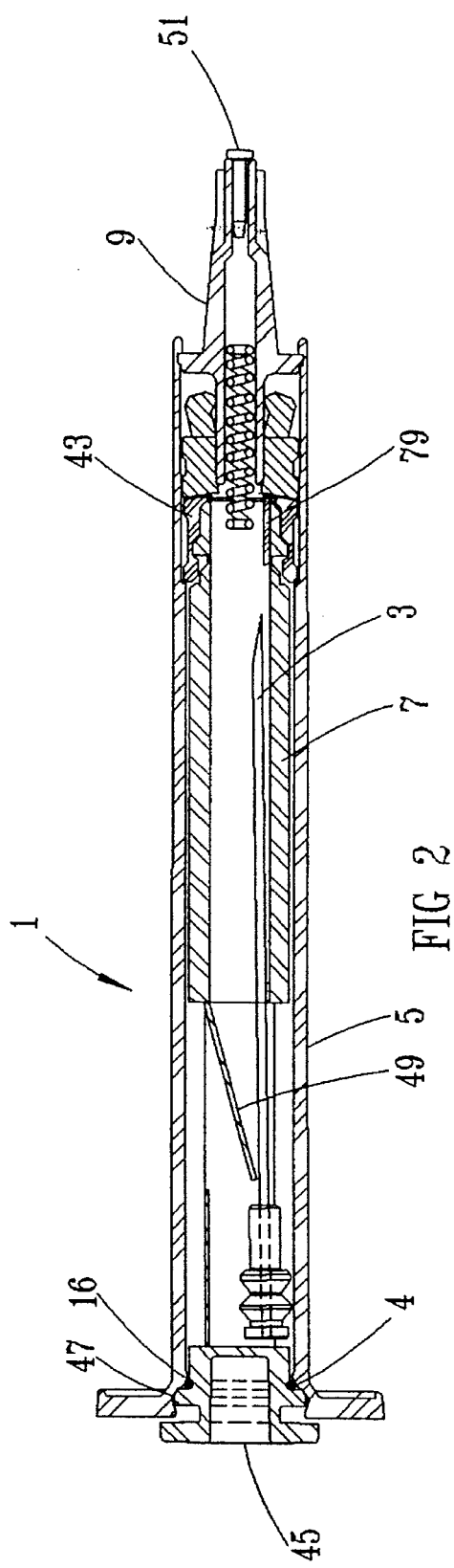

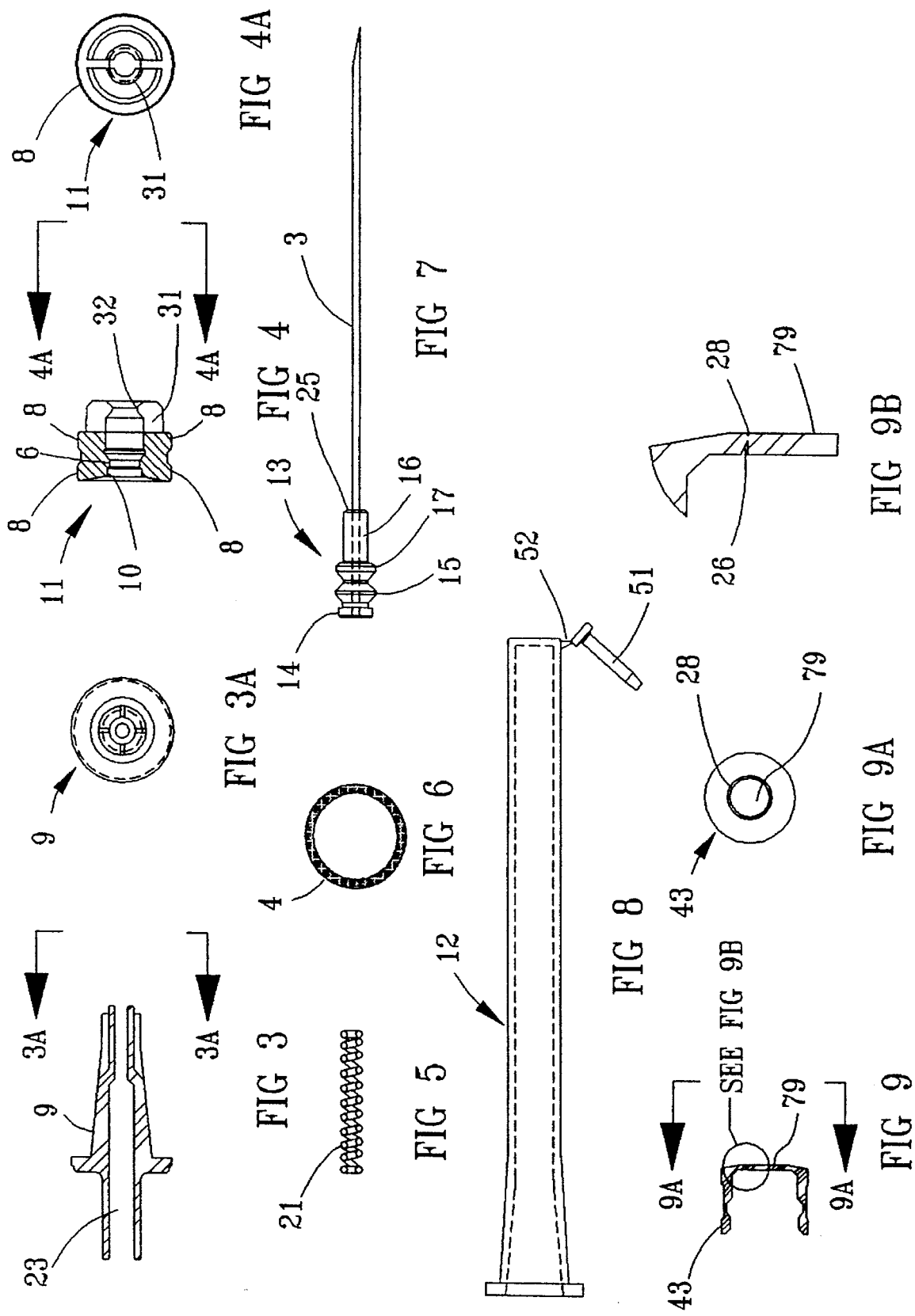

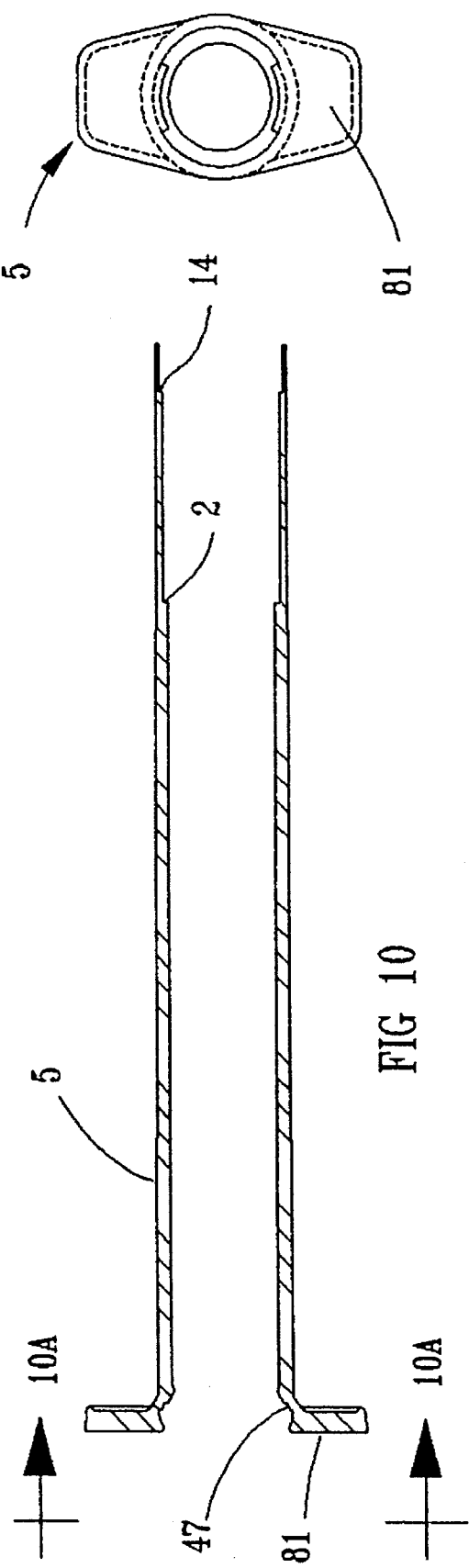
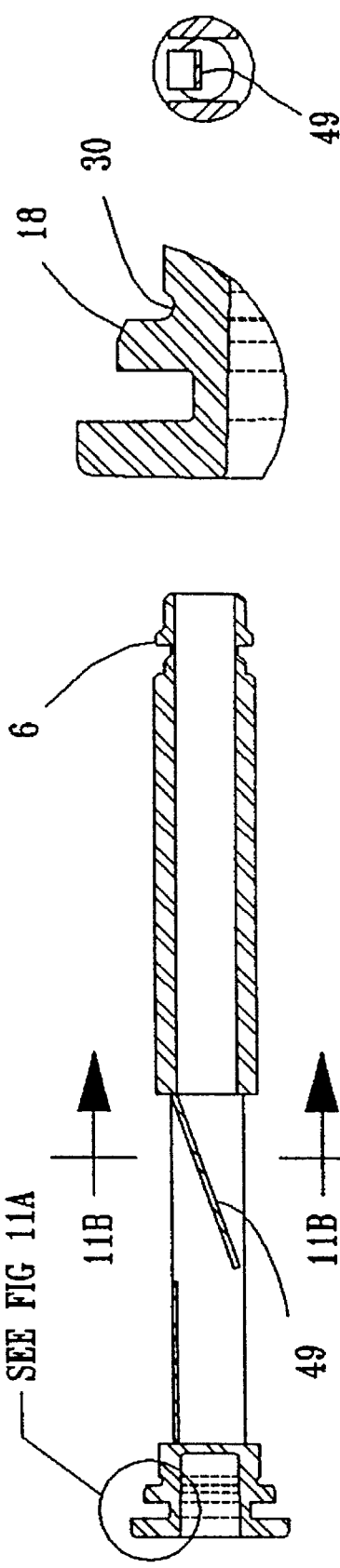

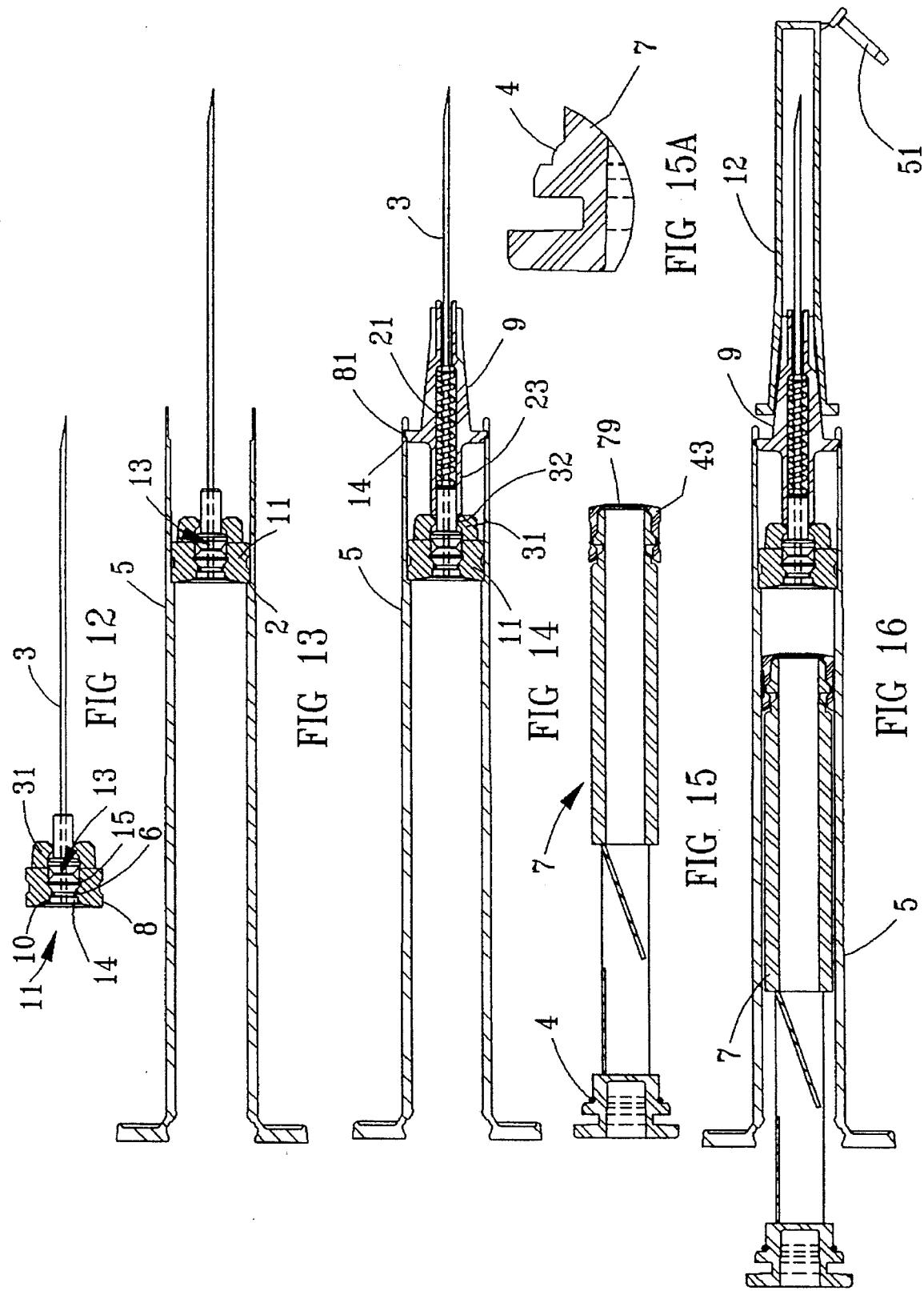

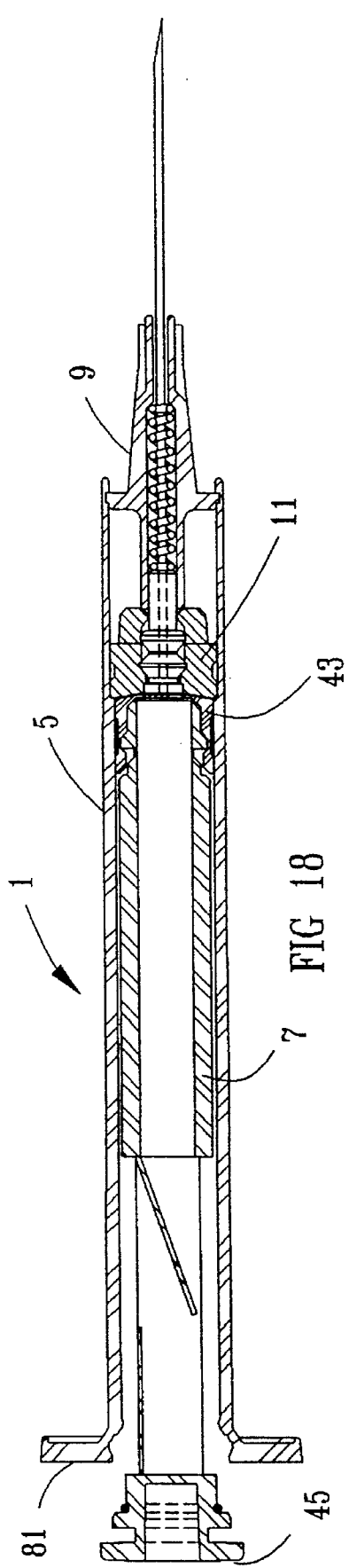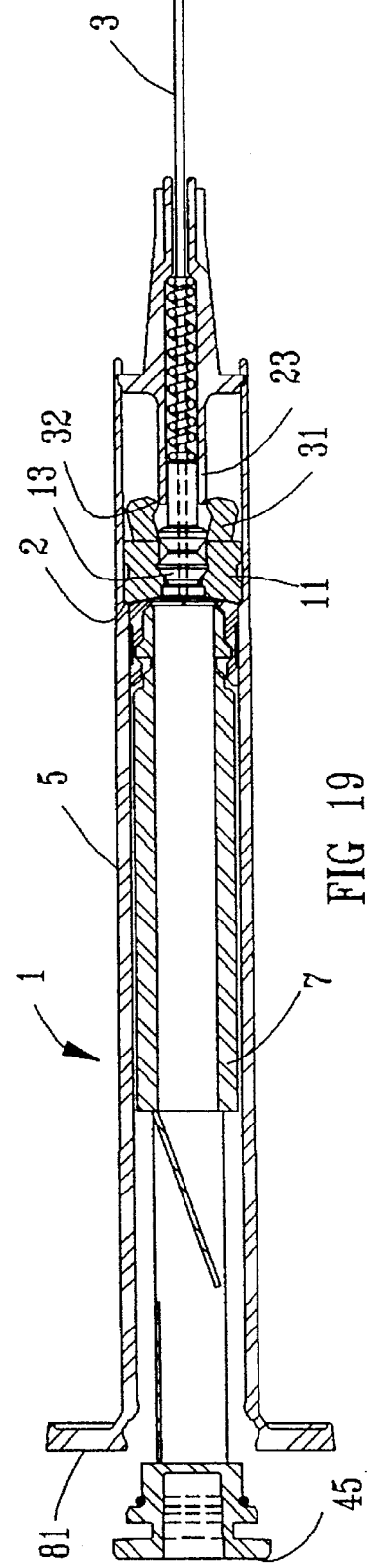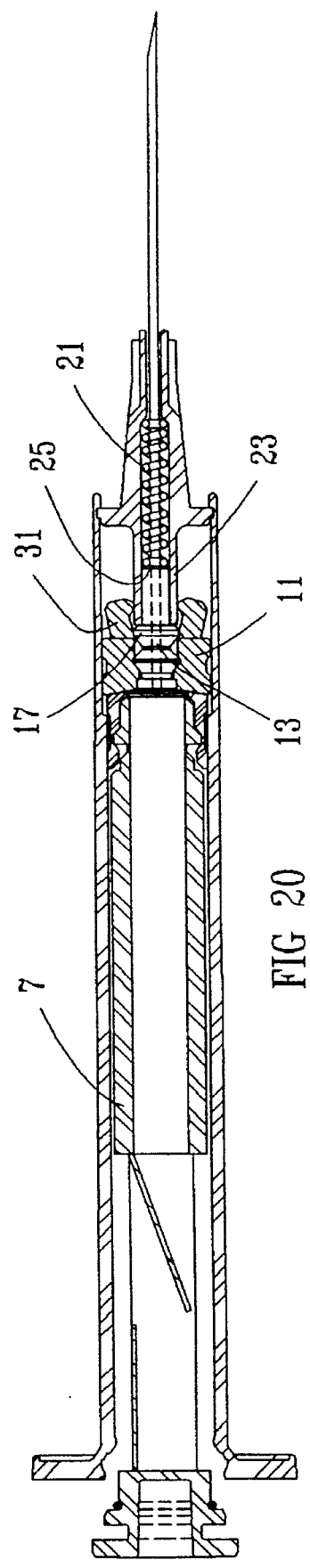

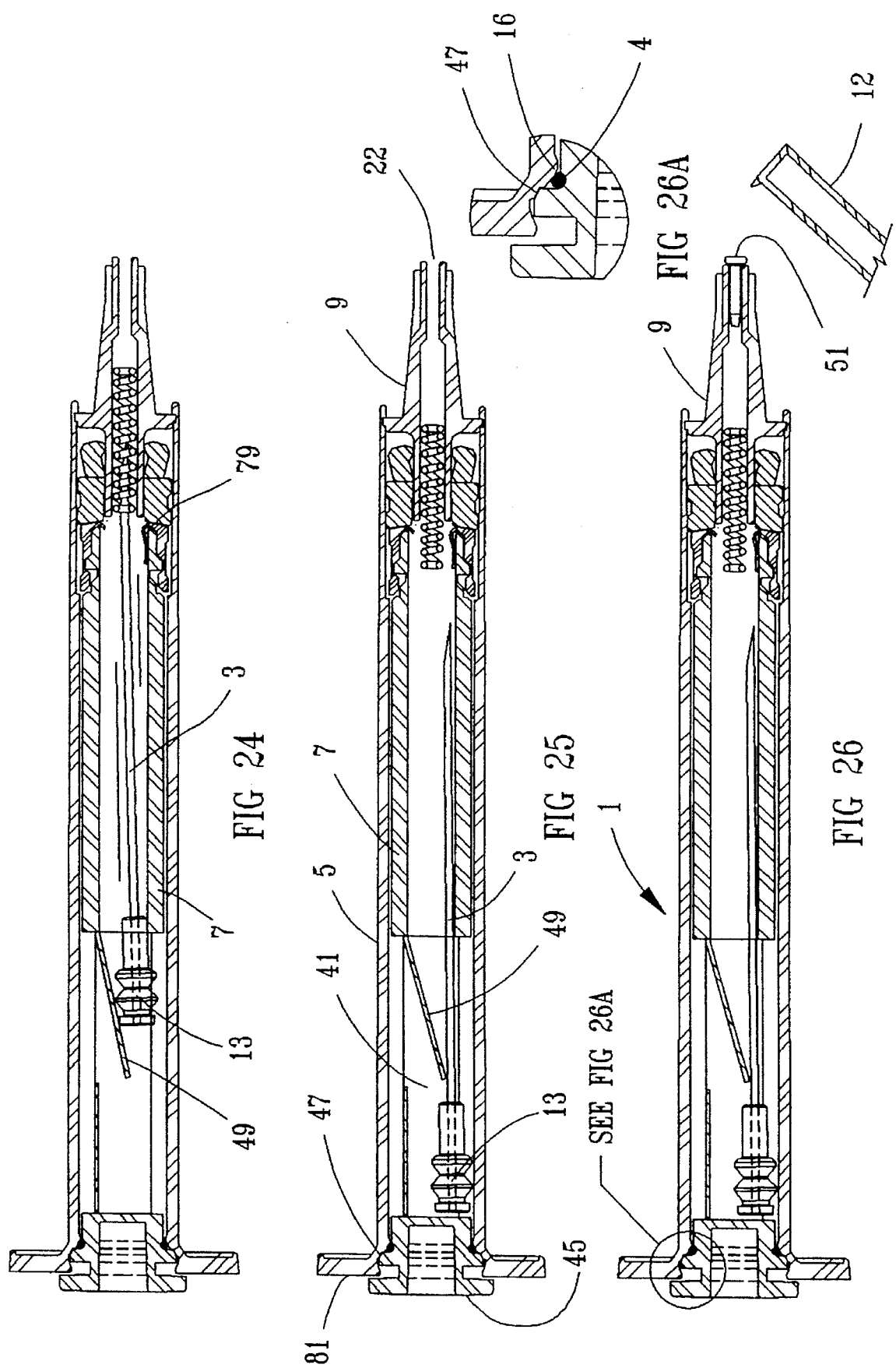

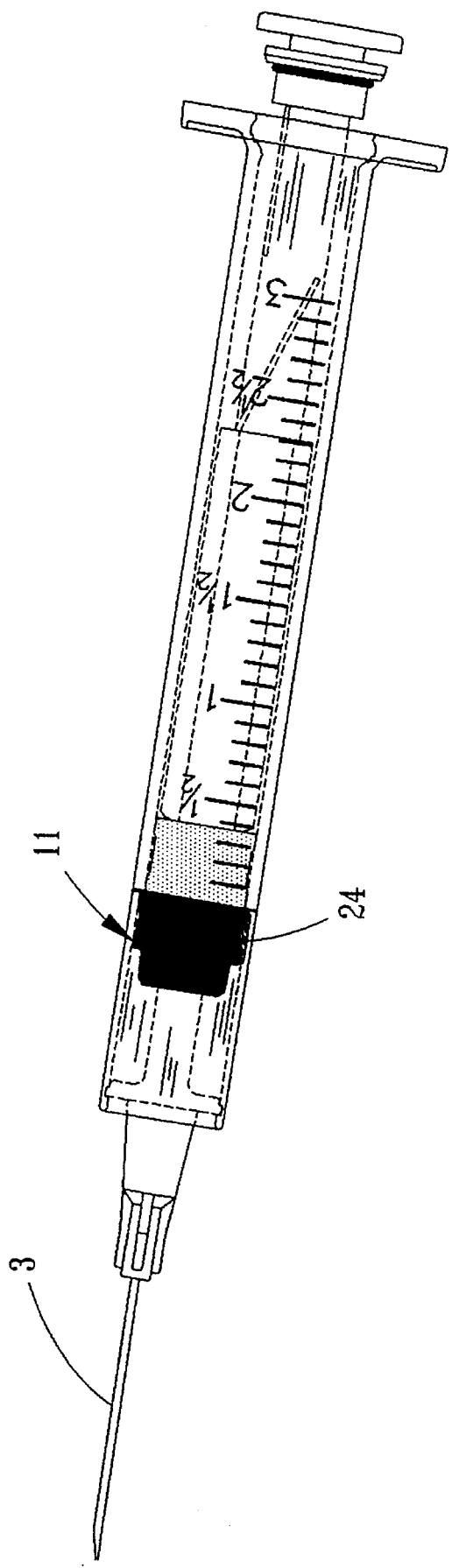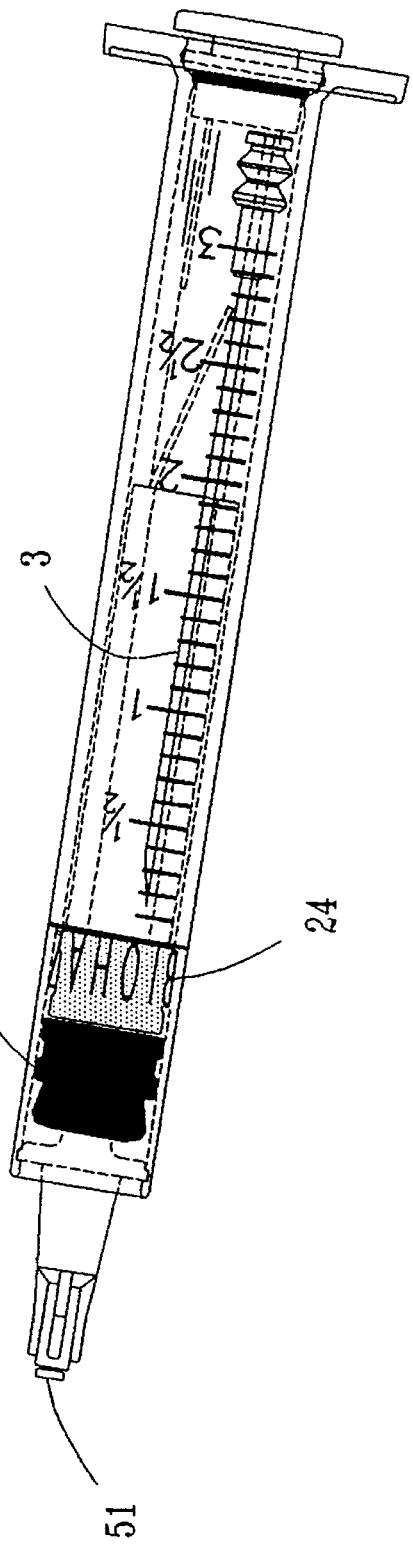
FIG 27
FIG 28

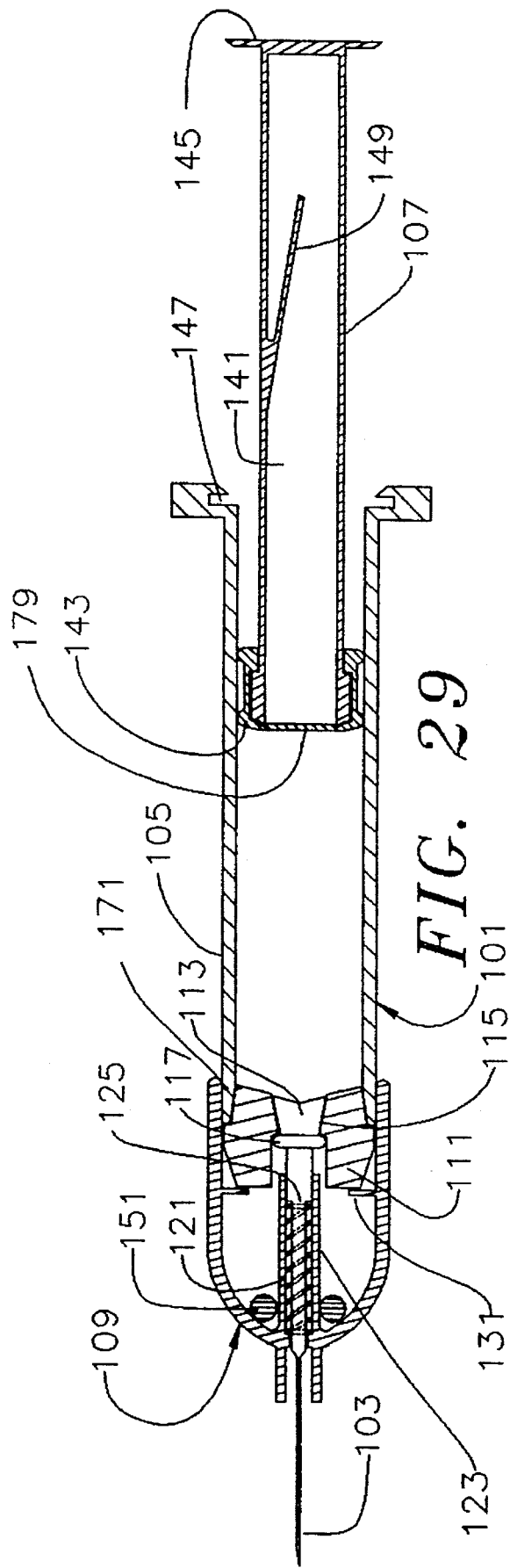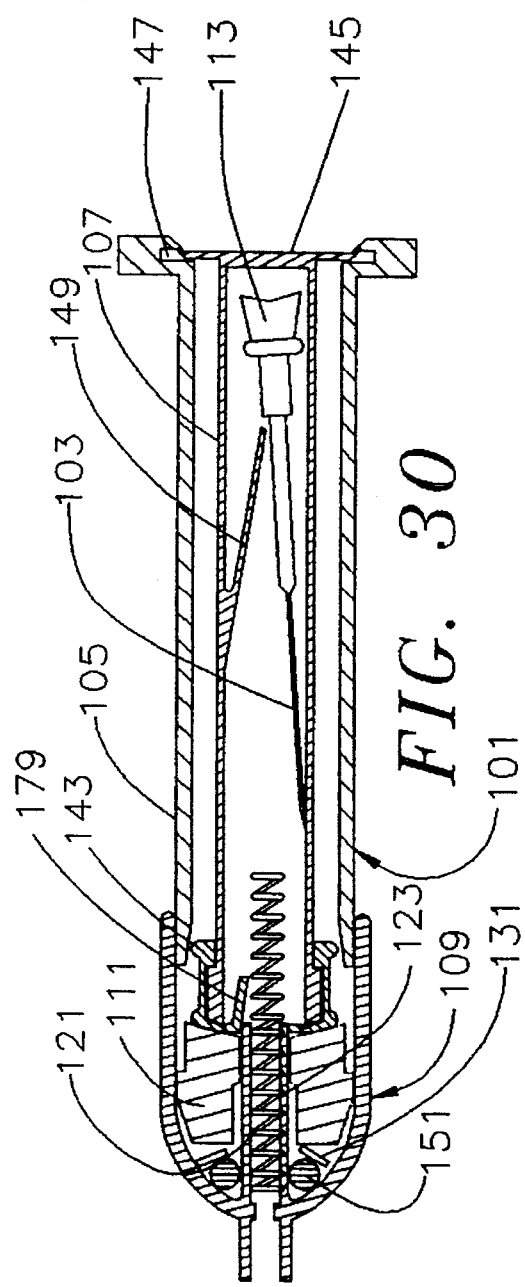

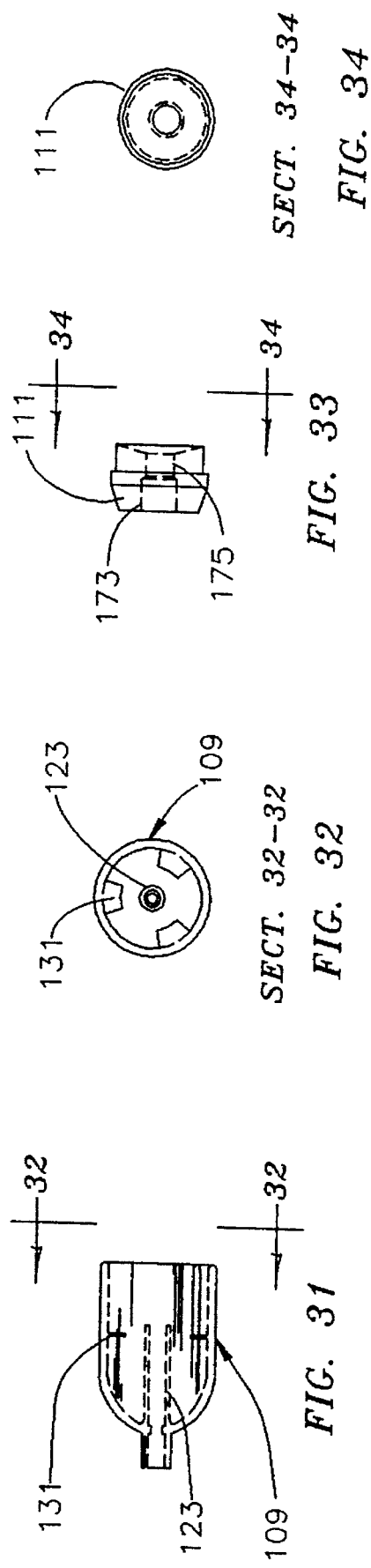
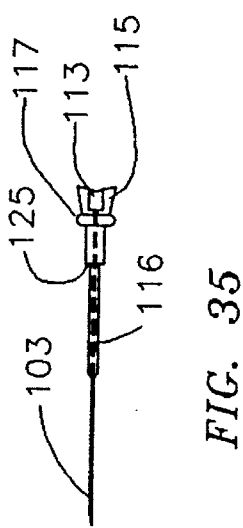

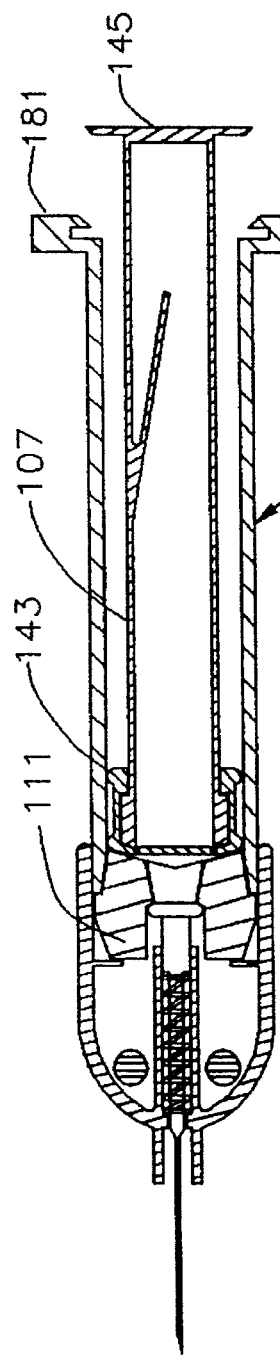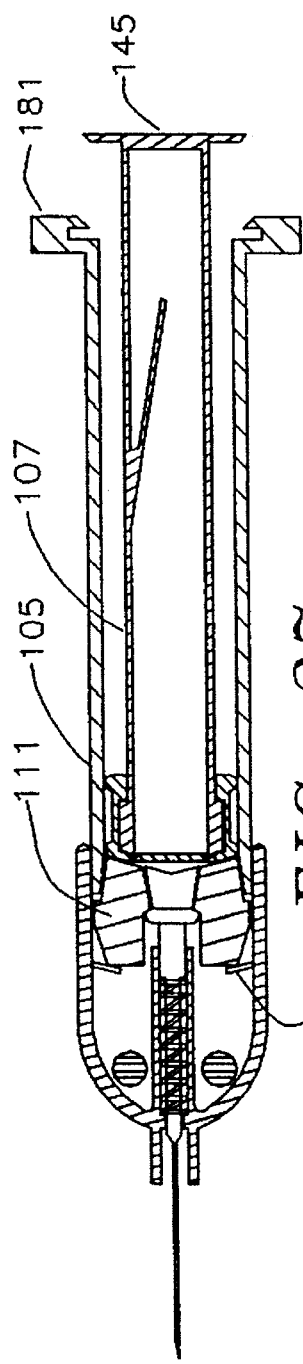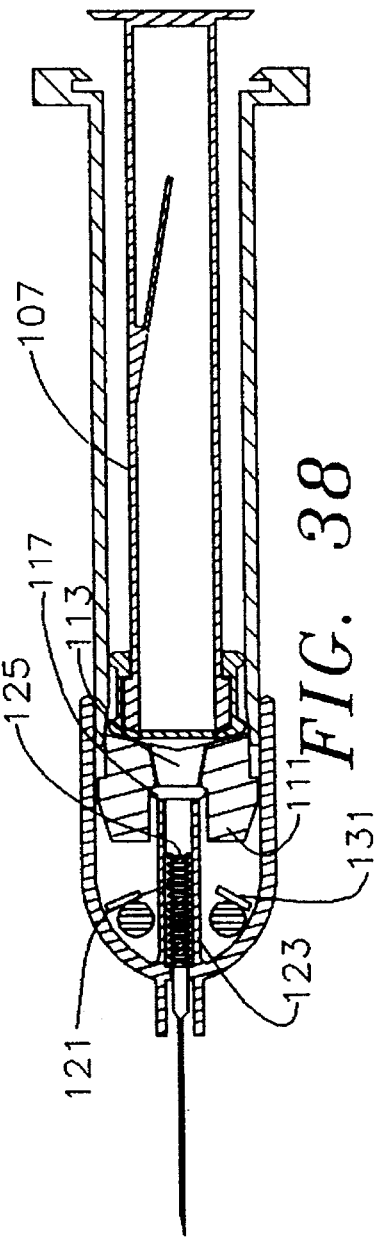

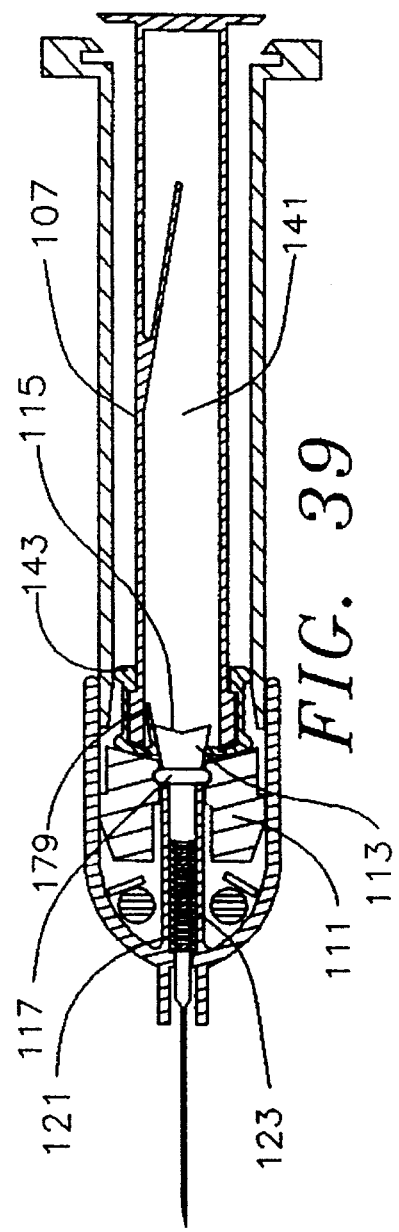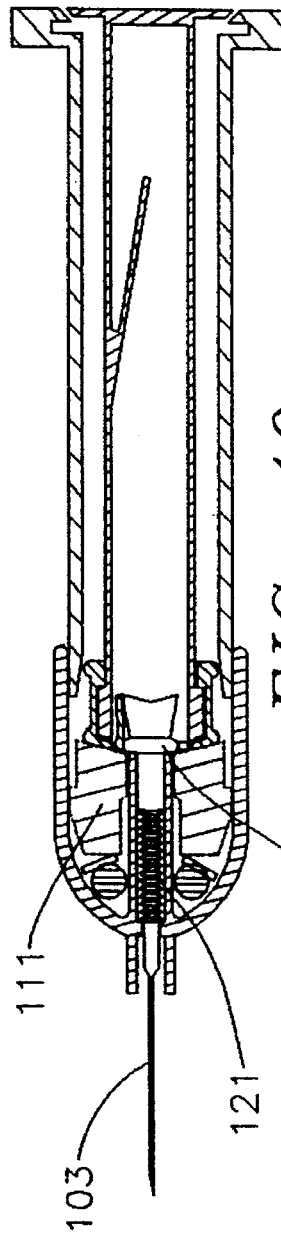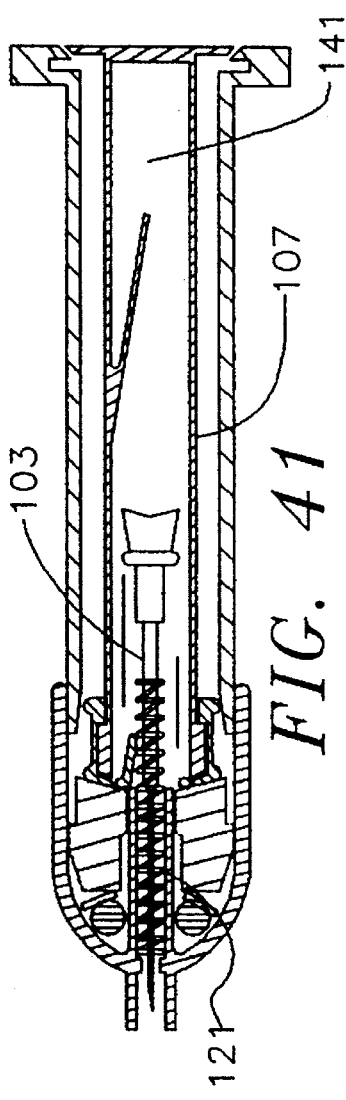

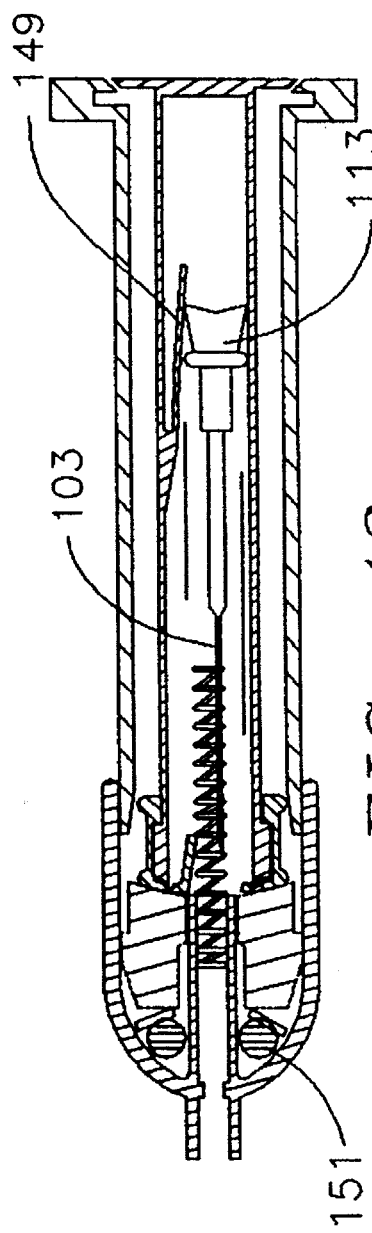
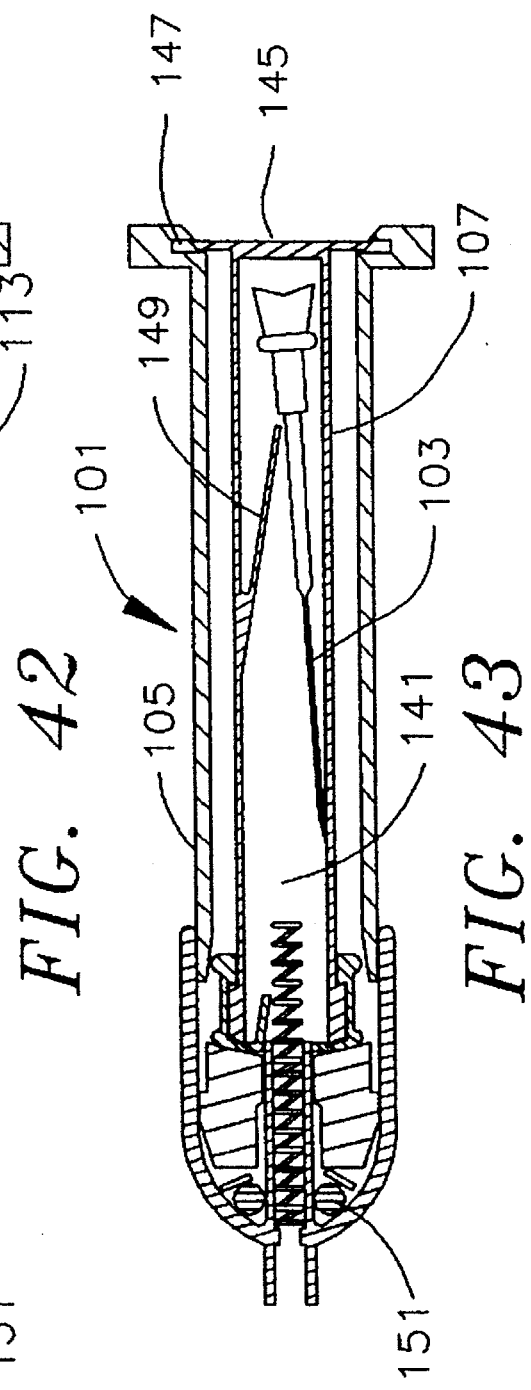

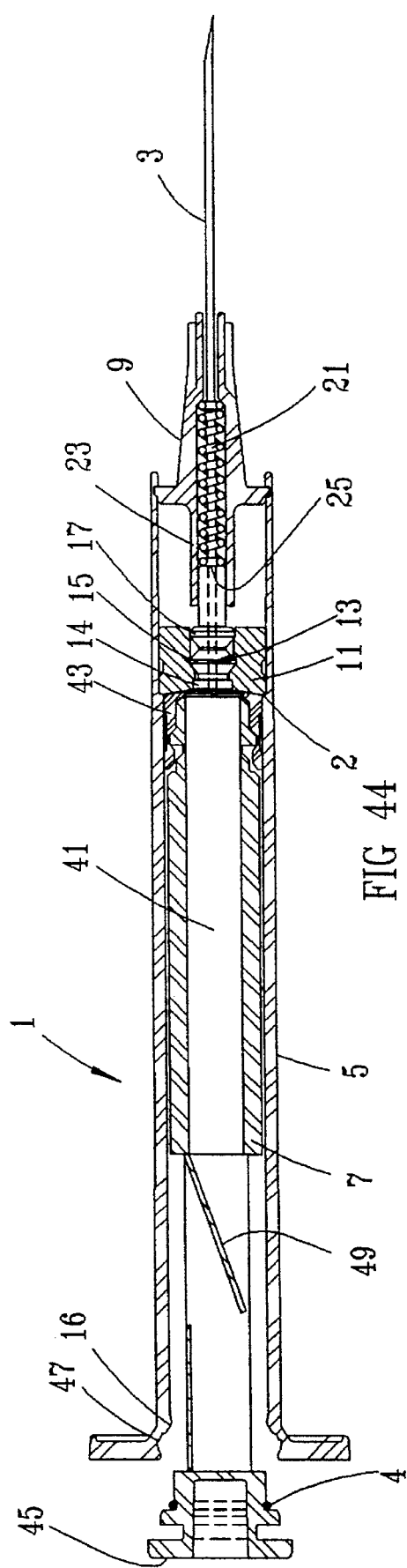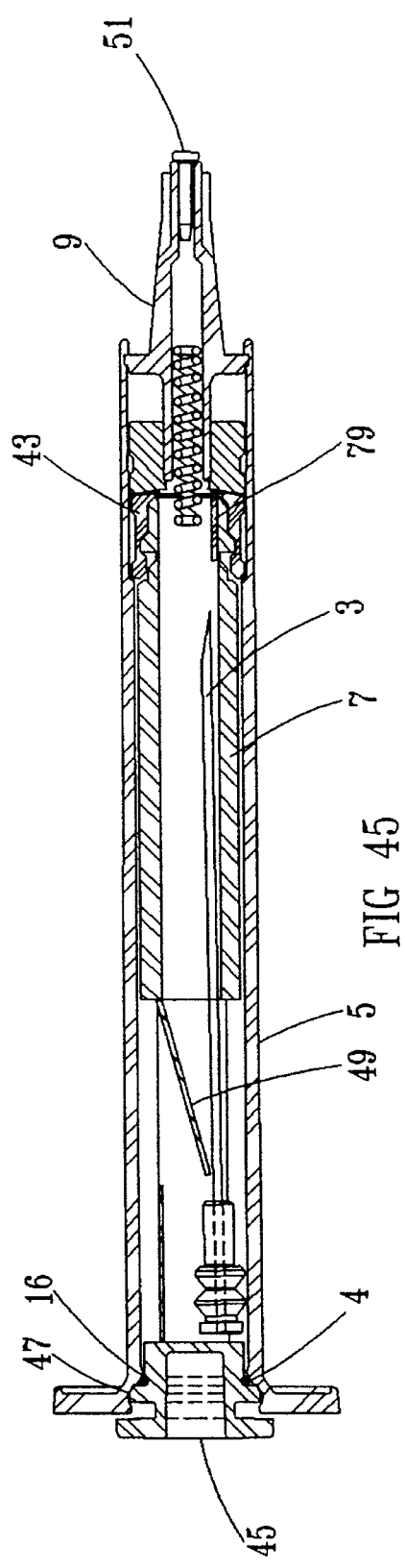

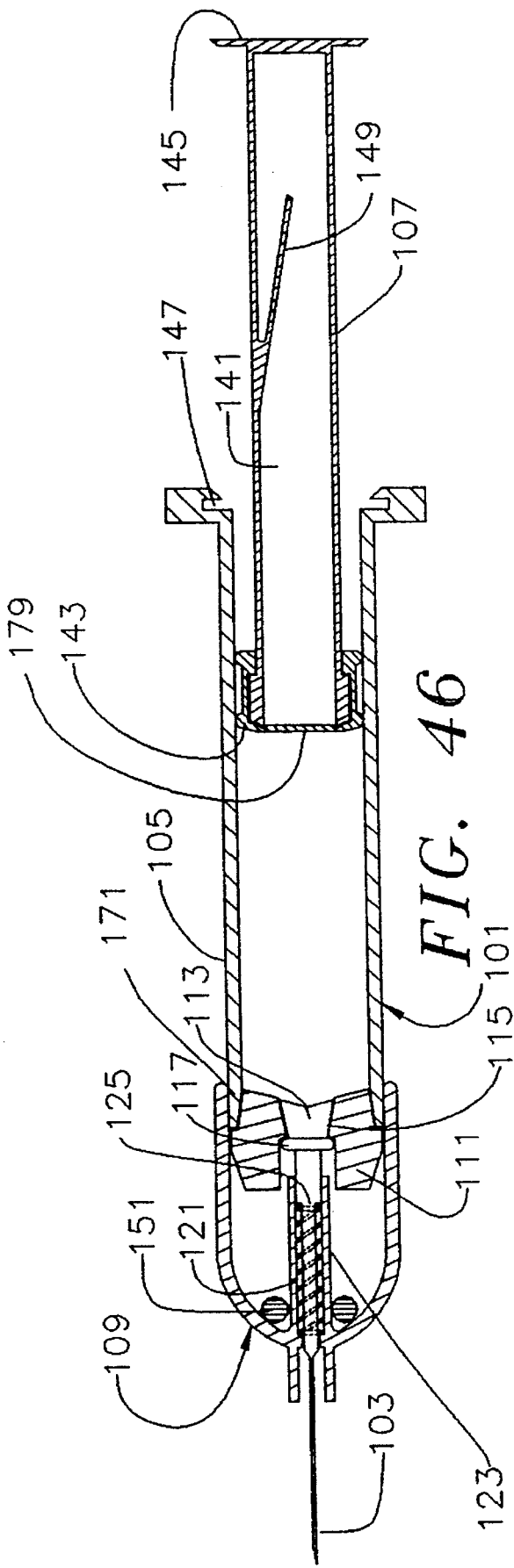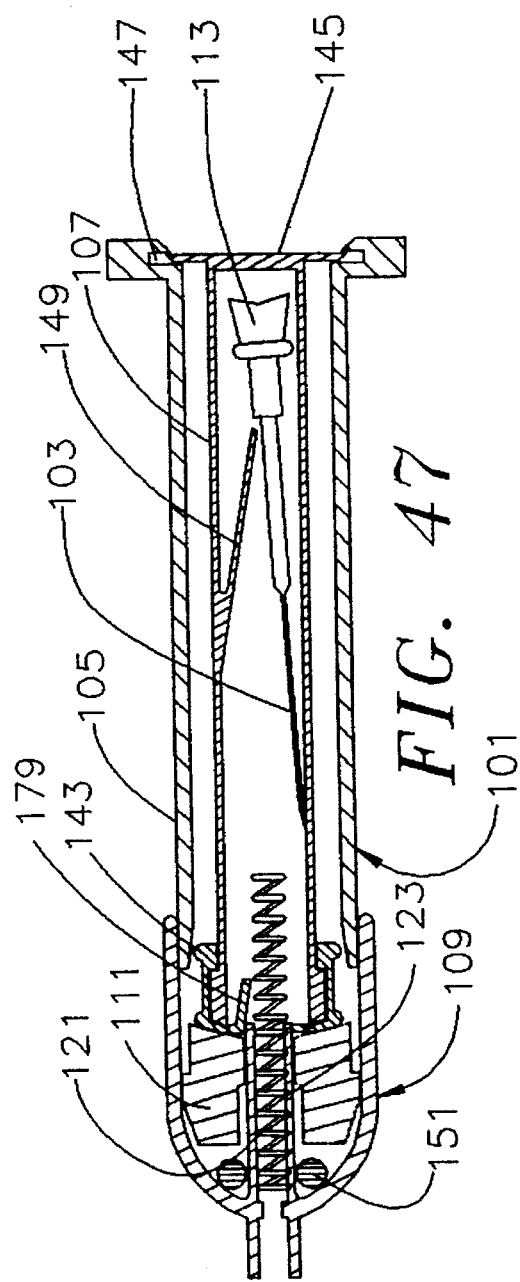
FIG. 46
FIG. 47

SAFETY SYRINGE

CROSS REFERENCE TO RELATED APPLICATIONS

This application is a continuation-in-part application from U.S. application Ser. No. 08/359,001 filed on Dec. 16, 1994 now abandoned which was a continuation of Ser. No. 07/813,115 which was filed on Dec. 23, 1991, now U.S. Pat. No. 5,211,629.

BACKGROUND OF THE INVENTION

This invention relates generally to the art of syringes and more particularly to a syringe which reduces the likelihood of unintentional puncture or pricking of human skin. In recent history, the transmission of contagious diseases, particularly those brought about exclusively by the co-mingling of human body fluids, has been of great technological interest. One of the particular problems has been associated with the use and disposal of hypodermic syringes, particularly among healthcare professionals. There have been various devices developed for the destruction of the needles or cannula used in such syringes. Additional devices have been developed for capping of syringes which attempt to minimize the likelihood of accidental puncture. The accidental puncture or pricking of a finger, or any other part of the body, after the treatment of a patient with a contagious disease, particularly a deadly contagious disease, results in a high likelihood of transmission of that disease. Various syringes have been developed in the prior art to attempt to minimize the likelihood of accidental puncture after patient treatment.

One such device is described in U.S. Pat. No. 4,973,316 to Dysarz wherein a needle is retracted into the barrel of the syringe after the use thereof. Another such device is described in U.S. Pat. No. 4,921,486 to DeChellis, et al. One of the earlier patents in this regard was U.S. Pat. No. 2,460,039 issued to Scherer, et al.

Other references disclosing devices relating to needle retraction in a syringe include U.S. Pat. No. 4,994,034 to Botich et al, U.S. Pat. No. 4,838,869 to Allard, and U.S. Pat. No. 5,114,410 to Batlle, GB 2 197 792 to Powers et al., WIPO 90/06146 to Nacci et al., and WIPO 90/03196 to Utterberg et al. While all such devices seek the same goal of preventing accidental puncture, considerable room for improvement exists.

SUMMARY OF THE INVENTION

It is thus an object of this invention to provide a novel hypodermic syringe which minimizes the likelihood of accidental puncture.

It is a further object of this invention to provide such a syringe which, after utilization, isolates the used needle so as to render such needle harmless, and automatically indicates that the syringe represents a biohazard.

It is a further and more particular object of this invention to provide such a hypodermic syringe which is operable utilizing only one hand.

It is a further and yet more particular object of this invention to provide such a syringe which automatically, upon the end of an injection, retracts its needle to prevent its reuse, while sealing the needle within the body of the syringe to prevent leakage of residual fluids.

It is a further object of the invention to provide a simple device, which is manufacturable in high volumes.

These as well as other objects are accomplished by a hypodermic syringe having a barrel with a plunger movable therein to inject a fluid through a hollow needle thereof. A hollow needle is housed in a passageway within a needle assembly. Positioned between the passageway within the needle assembly and a shelf on an internal wall of the syringe barrel is a deformable base, with integral flexible supports. The deformable base forms a liquid tight seal with the barrel, at the needle end of the barrel. The deformable base houses an enlarged head of the needle which enlarged head is in contact with energy storage means within the passageway in the needle assembly. The plunger has a thin, rupturable web on an end thereof which is part of a boot covering the end of the plunger, the boot, including the web, being liquid impermeable for forcing a liquid from the barrel upon movement of the plunger. Upon completion of an injection, the boot-covered plunger contacts the deformable base, and upon application of force at the plunger, moves such base downward. Continued application of force causes the flexible supports to flex and move over the needle assembly, permitting the deformable base to move the enlarged head of the needle downward until further movement of the enlarged head is blocked by the needle assembly. With the enlarged needle head blocked by the needle assembly, continued force at the plunger causes the deformable base to move around the enlarged needle head. As the deformable base moves around the needle assembly, the enlarged needle head begins to protrude from the deformable base and come into contact with the web on the boot of the plunger. Continued force causes the enlarged needle head to tear the web of the boot, positioning the enlarged needle head just inside a hollow portion of the plunger. The torn portion of the web creates a flap just inside the hollow plunger. As the plunger moves the deformable base still further, the enlarged needle head looses contact with the deformable base, which triggers a release of energy from the energy storage means in the passageway, projecting the needle with its enlarged head into the hollow portion of the plunger. Once inside the plunger, the needle is trapped by its enlarged head behind a flexible catch within the plunger. Final movement of the plunger causes the plunger to become substantially locked in the barrel and causes a liquid tight seal to be created between the plunger and the syringe body. A closing member placed on the front of the needle assembly completely seals the syringe to prevent residual fluids from escaping. Completion of the needle retraction also automatically highlights an indicia such as a biohazard label which alerts persons handling the device that the syringe has been used and represents a potential biohazard.

In an alternative embodiment of the syringe according to this invention, a barrel, needle assembly, needle head, and deformable base of different structures than above are utilized wherein the deformable base is positioned between sacrificial supports in the needle assembly and an internal wedged end of the barrel. Upon completion of injection, the boot contacts the deformable base, and upon application of force at the plunger, moves the base downward, initially breaking the liquid tight seal between the base and the barrel. Continued application of force causes the sacrificial supports within the needle assembly to sever, permitting the deformable base to move the enlarged head of the needle downward until further movement of the enlarged head is blocked by the passageway in the needle assembly. With the enlarged needle head blocked by the passageway, continued force at the plunger causes the deformable base to move around the enlarged needle head. As the deformable base moves forward, the enlarged needle head begins to protrude from the deformable base and come into contact with a thin, rupturable web on the boot of the plunger. Continued force causes the enlarged needle head to penetrate the web of the boot, positioning the enlarged needle head just inside a hollow portion of the plunger. As the plunger moves the deformable base still further, the enlarged needle head looses contact with the deformable base, which triggers a release of energy from the energy storage means in the passageway, projecting the needle into the hollow portion of the plunger. Once inside the plunger, the needle is trapped by its enlarged head within the plunger. Final movement of the plunger causes the plunger to become captured in the barrel at the back of the syringe.

BRIEF DESCRIPTION OF THE DRAWINGS

FIG. 1 of the drawings is a cross-sectional view of the syringe of this invention in its operational state.

FIG. 2 of the drawings is a cross-sectional view of the syringe of this invention in its post-operational state.

FIG. 3 is an isolated sectional view of the needle assembly of this invention.

FIG. 3A of the drawings is a cross-sectional view along line 3A—3A of FIG. 3.

FIG. 4 of the drawings is an isolated sectional view of the deformable base.

FIG. 4A is a cross-sectional view along line 4A—4A of FIG. 4 showing the cavity for the needle head and integral flexible supports.

FIG. 5 of the drawings is an elevational side view of the energy storage means.

FIG. 6 of the drawings is an elevational view of the plunger seal.

FIG. 7 of the drawings is an isolated view of the needle with it enlarged head.

FIG. 8 of the drawings is an elevational view of the needle guard, showing the needle assembly plug tethered to the tip of the needle guard.

FIG. 9 of the drawings is an isolated sectional view of the plunger boot of this invention.

FIG. 9A is a cross-sectional view along line 9A—9A of FIG. 9, showing the plunger-boot.

FIG. 9B is an enlarged sectional view of the encircled area of FIG. 9.

FIG. 10 of the drawings is an isolated sectional view of the barrel of this invention.

FIG. 10A is a cross-sectional view along line 10A—10A of FIG. 10.

FIG. 11 of the drawings is an isolated sectional view of a plunger in accordance with this invention.

FIG. 11A is an enlarged sectional view of the encircled area of FIG. 11.

FIG. 11B is a cross-sectional view along line 11B—11B of FIG. 11 illustrating needle capturing means.

FIGS. 12, 13, and 14 of the drawings are cross-sectional subassembly views illustrating assembly of the needle, enlarged head, base, barrel, needle assembly, and energy storage means.

FIG. 15 of the drawings is a cross-sectional view of the plunger of this invention, showing assembly of the plunger boot and the plunger seal on the plunger.

FIG. 15A of the drawings is a partial sectional view of the plunger showing an alternative embodiment for the plunger seal.

FIG. 16 of the drawings is a cross-sectional view of the completed assembly of the syringe.

FIGS. 18, 19, 20, 21, 22, 23, 24, 25, 26, and 26A of the drawings are cross-sectional views of the apparatus of this invention showing the sequence of operation, after the injection cycle.

FIG. 27 of the drawings is an elevational view of the syringe prior to needle retraction.

FIG. 28 of the drawing is an elevational view of the syringe subsequent to needle retraction wherein an indicia has been revealed.

FIG. 29 of the drawings is a cross-sectional view of an alternative embodiment of the syringe of this invention in its operational state.

FIG. 30 of the drawings is a cross-sectional view of the alternative embodiment of the syringe of this invention in its post-operational state.

FIG. 31 of the drawings is an isolated view of an alternative embodiment of the needle assembly of this invention.

FIG. 32 of the drawings is a cross-sectional view drawn along line 32—32 of FIG. 31.

FIG. 33 of the drawings is a side view of an alternative embodiment of the deformable base of this invention.

FIG. 34 of the drawings is a cross-sectional view drawn along line 34—34 of FIG. 33.

FIG. 35 of the drawings is a side view of the needle with an enlarged head of an alternative embodiment according to this invention.

FIGS. 36, 37, 38, 39, 40, 41, 42 and 43 of the drawings are sectional views of an alternative embodiment of the syringe of this invention illustrating the sequence of operation after the injection cycle.

FIGS. 44, 45, 46 and 47 of the drawings are sectional views of embodiments of a syringe where no supports are utilized.

DETAILED DESCRIPTION

Figure 17:
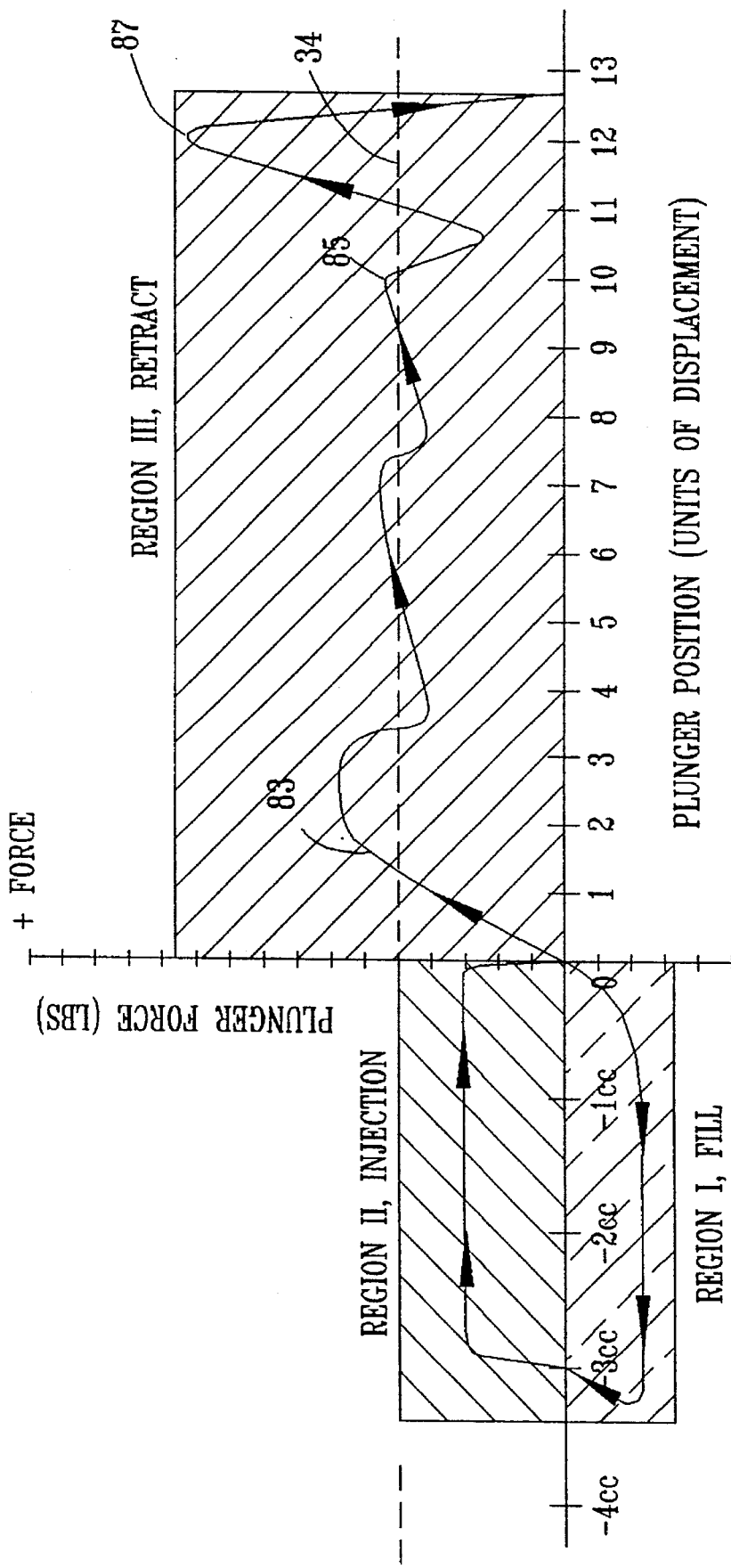
FIG. 17 of the drawings is a graph depicting the force/balance relationship upon which the syringe operation is based.

In accordance with this invention it has been found that a syringe may be provided for normal operation but, which upon completion of normal operation and continued movement of the plunger, results in a triggering of the needle or cannula to project such needle harmlessly into the plunger and body of the syringe.

Once trapped inside the plunger and body of the syringe, the needle is no longer subject to accidental pricking or poking of human tissue thus minimizing the likelihood of transfer of contagious disease which may be carried by fluids contained on the surface of or within such needle. To prevent possible leakage of residual fluids in the needle, the syringe can be sealed after use, and after such use an automatic indication is given that the syringe represents a biohazard. Various other advantages and features will become apparent from a reading of the following description given with reference to the various figures of drawing.

FIGS. 1 and 2 of the drawings illustrate the syringe 1 of this invention with the needle 3 illustrated in FIG. 1 in its normal pre-injection position. FIG. 2 of the drawings, however, shows the final position after operation of this invention wherein the needle 3 has been trapped and rendered harmless after the injection has taken place, and the plunger 7 has been locked within the barrel 5 of the syringe. The syringe 1 in accordance with this invention has relatively few components, which along with their function, will now be described with reference to the drawings in sequence beginning with FIG. 1.

The syringe 1 has a barrel 5 and a plunger 7 mounted therein. The needle 3 is contained within a needle assembly 9, which is fixed to barrel 5 by ultrasonic welding means or other permanent attaching means.

Needle 3 has an enlarged head 13, generally cylindrical in shape, positioned within and engaged by deformable base 11. Enlarged head 13 has a top 14, which is preferably flat and diametrically cylindrical. The top of enlarged head 13 can be concave in one embodiment. Below top 14 on enlarged head 13 are a plurality of diametrically wider areas or gradually extending bands, illustrated as areas 15 and 17, which are slightly wider than top 14. The bottom portion of enlarged head 13 is cylindrically smooth and defines a contacting portion 25 for contacting the energy storage means. By appropriately positioning the enlarged needle head 13 within deformable base 11 for a substantially mating engagement, the geometries of top 14 and area 15 of enlarged head 13 can be substantially mated and locked within deformable base 11 so that a liquid tight seal between needle head 13 and deformable base 11 is created at top 14 of enlarged head 13. As seen in FIG. 1, all of enlarged head 13 but a portion of the bottom portion is contained within the deformable base.

Needle assembly 9 has contained therein energy storage means, illustrated as spring 21, within a passageway 23, which is in contact with contacting portion 25. Deformable base 11 is positioned between barrel base shelf 2 and one end of needle assembly 9 wherein supports 31 of base 11 contact the end of the needle assembly.

Plunger 7 has a hollow 41 therein and has a boot 43 covering an end thereof which is fluid impermeable for forced movement of a fluid in barrel 5 during ordinary injection. A portion of boot 43 is illustrated as having been torn by the needle head in FIG. 2, with boot web 79 laying over in the front of plunger 7.

Preferably, plunger 7 has an enlarged thumb push 45 which, upon completion of a compression stroke, is substantially locked within a mating head portion 47 of barrel 5. As seen in FIG. 2 fitting plunger 7 within barrel 5 also produces a sealing action between plunger seal 4 and guard ring 16, preventing release of residual fluids at the back of the syringe, left in the needle after use. Plunger 7 has needle capturing means 49 therein which is illustrated in FIG. 2 as preventing the release of needle 3 from plunger 7. Also illustrated in FIG. 2 is closing member 51, illustrated as a plug, inserted into the front of needle assembly 9 to prevent residual fluids which may drain from needle 3, after the capture thereof, from leaking from the front of the syringe. It is envisioned according to this invention that various structures of closing members can be utilized, such as the plug as shown and also a capping member, as long as the opening left by needle retraction can be closed.

Reference will now be made to FIGS. 3 through 11B to more particularly illustrate the components of this invention as described above.

FIG. 3 is an isolated sectional view of needle assembly 9 of this invention. Passageway 23 is shown and is defined within needle assembly 9.

FIG. 3A of the drawings is a cross-sectional view along line 3A—3A of FIG. 3 illustrating the needle assembly 9 of this invention.

FIG. 4 is an isolated sectional view illustrating deformable base 11 which defines a passage therethrough for passage of the needle head, as discussed in more detail later. Deformable base 11 is designed to substantially matingly engage enlarged head 13. As seen in FIG. 4 base wedge 6 is provided, below where top 14 of enlarged head 13 can fit, for proper positioning of the needle in the deformable base. Further, cylindrical barrel seals 8 are provided to create proper sealing action between base 11 and barrel 5. The diameter and width of the barrel seals 8 can be made to create an optimum seal, while minimizing static and dynamic friction between base 11 and barrel 5. Also illustrated in FIG. 4 are supports 31, preferably formed as opposing, semicircular cantilevered beams projecting from the upper body 12 of base 11. Each support 31 has an inward engaging flange 32 for engaging a lower portion of enlarged head 13 and an end of the needle assembly, as shown in FIG. 1. Needle head seal 10 is further illustrated in FIG. 4 and is where top 14 of enlarged head 13 can fit. The diameter and width of needle head seal 10 is designed to provide optimum sealing with top 14, while minimizing static and dynamic friction between enlarged head 13 and base 11.

FIG. 4A of the drawings is a cross-sectional view along line 4A—4A of FIG. 4 illustrating deformable base 11. A preferred material for base 11 is an elastomer. Supports 31 are illustrated in the preferred embodiment as a pair of opposing, semicircular cantilevered beams, however, it is envisioned according to this invention that supports 31 could be connected and unitary or divided up further.

FIG. 5 of the drawings is an elevational side view of the energy storage means illustrated as spring 21.

FIG. 6 of the drawings is an elevational view of plunger seal 4 illustrated in one embodiment as an O-ring seal.

FIG. 7 of the drawings is an isolated view of needle 3, or cannula, with enlarged head 13. Top 14, wider areas 15 and 17, and contactor 25 on the bottom portion are illustrated. Also illustrated in phantom is the hollow portion 16 of the needle.

FIG. 8 shows a side view of a needle guard 12, with closing member 51 attached at the end thereof. Closing member 51 is attached or tethered by a breakable tab 52 which can be of plastic construction and which is broken to remove closing member 51. As illustrated, closing member 51 is preferably a plug which is attached by tab 52 to the needle guard at an angle wherein tab 52 connects to closing member 51 away from the end of closing member 51 which can be inserted or plugged into the needle assembly after needle retraction. As discussed above, the closing member of this invention can be of various types, such as a cap or a plug as shown, as long as the opening left by needle retraction can be closed. Preferably, the opening is closed off so that a liquid tight seal is obtained. The angular attachment of the closing member preferred herein and illustrated in figure 8 allows a person completing needle retraction to handle just the needle guard to insert the closing member into the needle assembly where the needle was positioned prior to retraction. Quite advantageously, this can be accomplished with the user's hands always positioned behind the opening in the needle assembly left as a result of needle retraction.

FIG. 9 is an isolated sectional view of boot 43 of this invention. FIG. 9A of the drawings is a cross-sectional view along line 9A—9A of FIG. 9 illustrating boot 43. FIG. 9B is an enlarged sectional view of the encircled area of FIG. 9. Referring to FIGS. 9, 9A and 9B, a thin, rupturable web 79 is shown as a portion of boot 43. To aid in the rupturing process of the web, tear groove 26 and tear groove 28, shown in figure 9B, are provided. The thickness of web 79 and the tear grooves are selected to withstand normal operating pressures within syringe 1, as shown in FIG. 1, but to allow relative ease in the puncturing of web 79 by enlarged needle head 13, shown in FIG. 6. The preferred material for boot 43 is an elastomer.

FIG. 10 is an isolated sectional view of barrel 5. FIG. 10A of the drawings is a cross-sectional view along line 10A—10A of FIG. 10 showing finger support flange 81 of barrel 5 of this invention. Referring to FIGS. 10 and 10A, at the finger support flange 81 of barrel 5 is shown an undercut 47 for locking the plunger into the barrel. At the opposite end of barrel 5, base shelf 2 and nose shelf 14 are illustrated. These internal offsets receive the base and the needle assembly respectively.

FIG. 11 of the drawings is an isolated sectional view of plunger 7 in accordance with this invention. Capturing means 49 is illustrated. Plunger boot termination 16 is also illustrated and is designed to receive rupturable boot 43.

FIG. 11A is an enlarged sectional view of the encircled area of FIG. 11 and illustrates cavity 30 for receiving plunger seal 4 and inclined surface 18 for fitting and substantially locking the plunger into the body of the syringe.

FIG. 11B is a cross-sectional view along line 11B—11B of FIG. 11 further illustrating needle capturing means 49.

Given the components described above, assembly in several primary steps is required to produce the syringe. FIGS. 12 through 16 illustrate these steps so as to result in a finished product. Needle 3 is first inserted into enlarged head 13. With reference to FIG. 12, the first assembly step is accomplished by inserting needle 3 into deformable base 11 between flexible supports 31 for a substantially mating engagement. Base wedge 6 is positioned between top 14 and wide area 15 of enlarged head 13 which blocks needle 3 movement in both directions. A liquid tight seal between enlarged head 13 and needle head seal 10 on base 11 as shown in FIG. 12 is created around the edge of top 14 of enlarged head 13. With needle 3 blocked into base 11, the next assembly step is accomplished.

In the next step of the assembly process, the subassembly in FIG. 12 is inserted into the front end of barrel 5 as shown in FIG. 13, until base 11 contacts and is positioned against base shelf 2. When base 11 is completely inserted as shown in FIG. 13, base 11 is compressed circumferentially in the direction of needle head 13, and a liquid tight seal is produced between base 11 and barrel 5.

To complete assembly of needle assembly 9 with barrel 5, as shown in FIG. 14, the energy storage means is first placed into passageway 23. The preferred embodiment of energy storage means is spring 21. Needle assembly 9 is then fixed to barrel 5 by threading needle 3 through the center of spring 21 in passageway 23 and inserting needle assembly 9 into the front of barrel 5, until needle assembly 9 contacts and is positioned against nose shelf 14. Permanently joining needle assembly 9 and barrel 5 can be accomplished by ultrasonic welding around the circumference of barrel 5 at overlap 81, or any other permanent attaching means can be utilized. Attachment of needle assembly 9 to barrel 5 creates a liquid tight seal between the two parts. As a result of this assembly step, the end of needle assembly 9 is positioned just in contact with engaging flanges 32 of supports 31, thus preventing movement of base 11 and needle 3 contained therein for normal syringe use.

In the final step of assembly, plunger seal 4 and boot 43 are placed onto plunger 7 as shown in FIGS. 15. Boot 43 is preferably placed onto plunger 7 so that web 79 is just at the end of the plunger. Plunger 7 is then inserted into barrel 5. FIG. 15A is a partial sectional view of the end of the plunger with a plunger seal showing an alternative embodiment wherein the plunger seal is formed as an integral and unitary part of the plunger so that the seal as provided by use of an O-ring is accomplished by forming the ring as an integral part of the plunger. To complete the assembly as shown in FIG. 16, needle guard 12 is placed on needle assembly 9, with closing member 51 tethered at the tip of needle guard 12. It will be apparent to those in the art that there exists other possible sequences of assembly other than those described herein that can be used to produce the completed assembly as shown in FIG. 16, producing the same syringe ready for operation.

The syringe operates on a "force/balance" principal as depicted in the graph of FIG. 17. In the graph normal operation is represented by regions I and II. In these regions limited positive and negative forces are applied between the plunger 7 and body 5, shown in FIG. 18, for normal operating functions of filling the syringe and for injections. Positive forces are defined as forces which move the plunger into the syringe body, while negative forces are defined as those forces which pull the plunger from the syringe body. Typical "filling" and "injection" cycles are depicted in regions I and II, respectively. As long as the positive force applied between the plunger 7 and body 5 of syringe 1 is below threshold 34, base 11 balances the operating force and remains in its assembled position, as shown in FIG. 18. But, for positive forces applied to the syringe above threshold 34, base 11 becomes unbalanced and begins to move in the direction of needle assembly 9. Once force above threshold 34 is applied and maintained, operation of the syringe moves into region III, where the needle is retracted into the plunger of the syringe. In region III, points 83, 85 and 87 represent a typical device where base 11 first begins to move, needle head 13 is released and plunger 7 becomes substantially locked into body 5 respectively.

The sequence of operation will now be described with regard to FIG. 1 and FIGS. 18 through 28. As can be seen, FIG. 1 is a cross-sectional view of safety syringe 1. For normal syringe operating forces, safety syringe 1 operates as any conventional syringe. For use, the syringe is filled from an ampule in a normal manner, as standard procedure dictates. Once filled, the injection cycle is accomplished, again according to standard practice. At completion of the injection cycle, plunger boot 43 is just mating with base 11, as shown in FIG. 18, and all fluids, which can be, are expended from syringe 1 through the needle. Before the syringe is released or discarded, by the user, the needle retraction cycle should be accomplished.

At the beginning of the needle retraction cycle, syringe 1 is usually held between the index finger and the middle finger at support flange 81, with the thumb resting on thumb push 45, presumably the same as the syringe was held at completion of the injection cycle. Plunger 7 is contacting base 11 at boot 43, as shown in FIG. 18.

With reference to FIG. 19, force is applied between finger support flange 81 and thumb push 45. This force is transmitted along plunger 7 to deformable base 11 and supports 31. As the force increases sufficiently supports 31 begin to flex open away from one another as shown in FIG. 19, wherein engaging flanges 32 move away from and lose contact with the enlarged needle head 13 and flex open just enough to pass over passageway 23 and to allow further movement of base 11 and needle 3 toward an end of the barrel.

As shown in FIG. 20, the continued application of force applied to plunger 7 continues to cause supports 31 to ride up on and around the needle assembly as deformable base 11 moves further. As the deformable base and the enlarged needle head are forced toward the end of the barrel, the bottom portion of enlarged head 13, which extends partially into the needle assembly prior to the retraction process, is forced further into the needle assembly, until wide area 17 contacts the end of the needle assembly and prevents any further movement of the enlarged head into the needle assembly by its greater diameter than passageway 23 within the needle assembly. This allows the plunger to force the base to deform and pass around the now stationary enlarged needle head. Spring 21 is fully compressed in the process by contactor 25 of the needle head.

Figure 21:
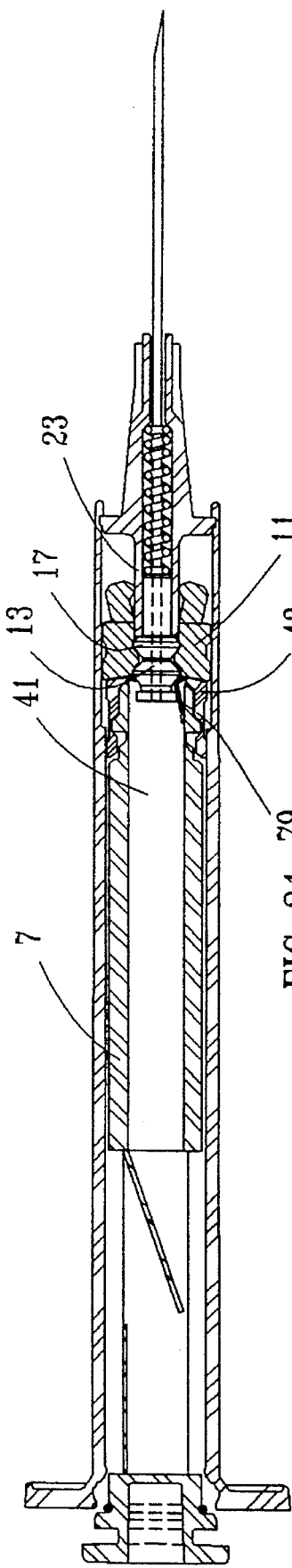

With reference now to FIG. 21, as deformable base 11 moves further toward the end of the barrel, needle head 13 begins to protrude from base 11 and come into contact with web 79 of boot 43 on plunger 7. Continued force causes further translation of base 11 and needle head 13 to tear web 79 of boot 43, positioning enlarged needle head 13 just inside hollow 41 of plunger 7 while wide area 17 remains embedded within deformed base 11, as shown in FIG. 21.

Figure 22:
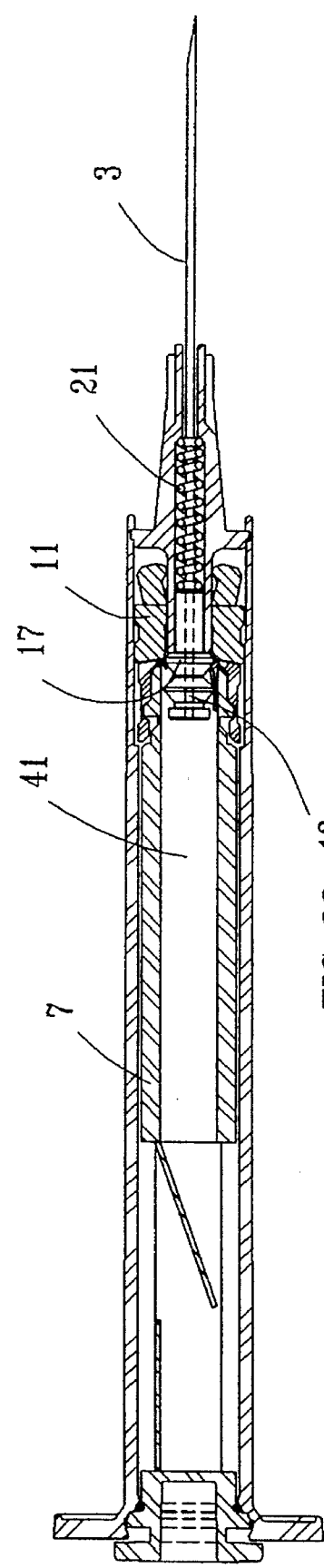
Figure 23:
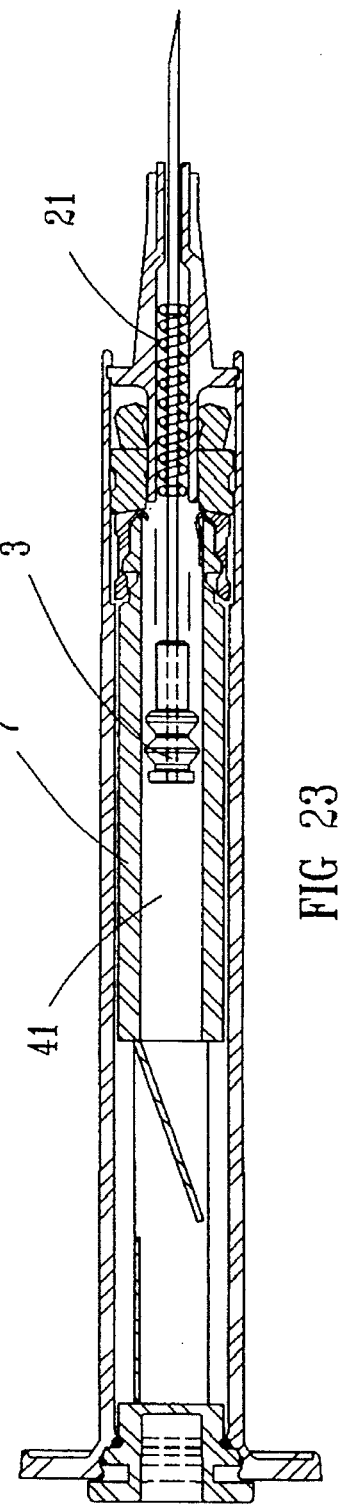

With reference to FIG. 22, continued translation of deformable base 11 causes wide area 17 to eventually lose contact with deformable base 11, creating a trigger-like release of enlarged head 13. Upon this trigger-type action, energy stored within spring 21 is released and imparted to needle 3 to project needle 3 into hollow 41 of plunger 7, as illustrated in figure 23.

Referring now to FIG. 24, it is seen that needle 3, at its enlarged head 13, contacts capturing means 49 which is a flexible catch that elastically flexes to permit enlarged needle head 13 to pass through the constriction formed by capturing means 49 and an inner wall of plunger 7. This is further illustrated in FIG. 25 where needle head 13 is shown having passed capturing means 49 and being captured within hollow 41 of plunger 7 wherein the needle head will move back past the capturing means. At this point, it should be noted that plunger 7 has been matingly and substantially locked within barrel 5 by mating head portion 47 engaging a portion of the plunger near thumb push 45. As shown in FIG. 26A, a liquid tight seal between plunger seal 4 and guard ring 16 is created.

To finish the operational sequence, closing member 51 tethered to the end of needle guard 12, can be inserted into opening 22 of needle assembly 9 as shown in FIG. 26 and described with reference to FIG. 8. Closing member 51 can be forced into position by pressing it against a heavy, solid object. Once closing member 51 is lodged into position, closing member 51 can be separated from needle guard 12 with a twisting action, leaving syringe 1 as shown in FIG. 26. This closure process can therefore be advantageously accomplished with a user's hands always remaining behind the opening left by the retracted needle.

As a result of accomplishing the needle retraction cycle as described, syringe 1 is left as shown in FIG. 26. Also preferably accomplished during the needle retraction cycle is revelation and amplification of an indicia or label such as biohazard label 24, as shown in FIG. 28. Before the needle retraction cycle, base 11 is under biohazard label 24 as seen in FIG. 27 wherein the label is not readable. It is preferred that biohazard label 24 be printed in black, or any other appropriate color, and that base 11 also be the same or substantially similar color so that biohazard label 24 is unnoticeable to the user. It is also preferred that boot 43 be of a different, contrasting color. After the needle retraction cycle, base 11 is no longer left under the biohazard label, and boot 43 is under the label, as shown is FIG. 28. Since boot 43 is any appropriate highly contrasting color relative to base 11 and the biohazard label, such as orange when the other two are black, biohazard label 24 is significantly revealed and amplified and becomes very noticeable to the user or other people, as shown in FIG. 28.

FIGS. 29 and 30 of the drawings illustrate the syringe 101 of this invention with the needle 103 illustrated in figure 29 in its normal pre-injection position. FIG. 30 of the drawings, however, shows the net result of this invention wherein needle 103 has been trapped and rendered harmless after the injection has taken place, and the plunger has been locked within the barrel of the syringe. Syringe 101 in accordance with this invention is similar to syringe 1 described above and has relatively few components. Components of syringe 101 that are different from syringe 1 above are the deformable base, the enlarged needle head, and the needle assembly and the barrel.

Syringe 101 has a barrel 105 and a plunger 107 mounted therein. Needle 103 is contained within a needle assembly 109, which is fixed to barrel 105 by ultrasonic welding means or other permanent attaching means.

Needle 103 has an enlarged head 113 mounted within deformable base 111. Enlarged head 113 has a wedge portion 115 and a circular flange portion 117. By appropriately positioning the enlarged head 113 within deformable base 111, the geometries of the flange portion and wedge portion of enlarged head 113 substantially lock such enlarged head portion within the deformable base, while also creating a liquid tight seal between needle head 113 and deformable base 111.

Needle assembly 109 has contained therein energy storage means, illustrated as spring 121 within a passageway 123. Enlarged needle head 113 has a contacting portion 125 which contacts energy storage means 121. Sacrificial supports 131 position deformable base 111 within needle assembly 109.

Plunger 107 has a hollow 141 therein and is terminated by a boot 143 having a rupturable web 179, the boot being fluid impermeable for movement of a fluid in the barrel during ordinary injection. Web 179 of boot 143 is illustrated as having been ruptured in FIG. 30.

Preferably, plunger 107 has an enlarged compression section at thumb push 145 which, upon completion of a compression stroke, is locked within a mating head portion 147 of barrel 105. Plunger 107 has needle capturing means 149 therein which is illustrated in FIG. 30 as preventing the release of needle 103 from plunger 107. Also illustrated in FIGS. 29 and 30 is an absorption means 151, such as cotton, to collect any fluids which may drain from needle 103 after the capture thereof.

FIG. 31 of the drawings is an isolated view of needle assembly 109 of this invention. Sacrificial supports 131 and passageway 123 are illustrated in partial phantom.

FIG. 32 is a cross-sectional view along the line 32—32 of FIG. 31, further illustrating sacrificial supports 131 and passageway 123 within needle assembly 109.

FIG. 33 of the drawings is a side view of deformable base 111. A preferred material for base 111 is an elastomer. As seen in FIG. 33, counterbore 173 and thrubore 175 are provided for proper positioning of the needle in the deformable base.

FIG. 34 is a cross-sectional view along the line 34—34 of FIG. 33 further illustrating deformable base 111.

FIG. 35 of the drawings is a side view of needle 103 or cannula. Contactor 125, circular flange 117 and enlarged head 113 with wedge portion 115 are illustrated. Also illustrated in phantom is the hollow portion 116 of the needle.

The sequence of operation of syringe 101 will now be described with regard to FIG. 29 and FIGS. 36 through 43. As can be seen, FIG. 29 is a cross-sectional view of safety syringe 101. For normal syringe operating forces safety syringe 101 operates as any conventional syringe. For use, the syringe is filled from an ampule in a normal manner, as standard procedure dictates. Once filled, the injection cycle is accomplished, again according to standard practice. At completion of the injection cycle, plunger 107 is just mating with base 111, as shown in FIG. 36, and all fluids, which can be, are expended from syringe 101. Before the syringe is released, or discarded, by the user, the needle retraction cycle should be accomplished.

At the beginning of the needle retraction cycle, syringe 101 is usually held between the index finger and the middle finger at support flange 181, with the thumb resting on thumb push 145, presumably the same as the syringe was held at completion of the injection cycle. Plunger 107 is just mated with base 111 at boot 143, as shown in FIG. 36.

With to FIG. 37, force is applied between finger support flange 181 and thumb push 145. This force is transmitted along the plunger to deformable base 111 and sacrificial supports 131. As the force increases sufficiently, the liquid tight seal between barrel 105 and deformable base 111 is broken, and sacrificial supports 131 begin to fracture.

As shown in FIG. 38 further force is applied at plunger 107. Sacrificial supports 131 are severed and deformable base 111 moves forward, further compressing energy storage means 121. Deformable base 111 moves forward until circular flange 117, on needle head 113 which is in translation with base 111, comes into contact with the end of needle passageway 123.

With reference now to FIG. 39 enlarged needle head 113 is blocked by passageway 123, and continued force at plunger 107 causes deformable base 111 to deform and move around circular flange 117 on enlarged needle head 113 as deformable base 111 moves forward, enlarged needle head 113 begins to protrude from base 111 and come into contact with rupturable web 179 of boot 143, positioning enlarged needle head 113 just inside hollow 141 of plunger 107 while circular flange 117 remains embedded within deformed base 111, as shown in FIG. 39.

With reference to FIG. 40, continued translation of deformable base 111 causes circular flange 117 to eventually lose contact with deformable base 111, creating a trigger-like release of circular flange 117. Upon this trigger-type action, energy stored within spring 121 is released and imparted to needle 103 to project needle 103 into hollow 141 of plunger 107, as illustrated in FIG. 41.

Referring now to FIG. 42, it is seen that needle 103, at its enlarged head 113, contacts capturing means 149 which deforms to permit enlarged head 113 to pass through the constriction formed by capturing means 149. This is further illustrated in FIG. 43 where needle 103 is shown captured within hollow 141 of plunger 107. At this point, it should be noted that plunger thumb push 145 has been locked within the mating section 147 of barrel 105. As syringe 101 is tilted downward, fluids remaining in needle 103 flow within hollow 141, down the exterior side of passageway 123 to absorbent means 151 where the fluids are absorbed and prevented from being released from the interior of syringe 101.

FIGS. 44 and 45 of the drawings illustrate syringe 1 of this invention wherein the flexible supports are not utilized. It has been found according to this invention that syringe 1 can function to retract the needle without supports 31 when small syringes, such as 1 cc syringes are used.

FIGS. 46 and 47 of the drawings illustrate syringe 101 of this invention wherein sacrificial supports 131 are not utilized. It has been found according to this invention that syringe 101 can function to retract the needle without sacrificial supports 131 when small syringes, such as 1 cc syringes, are used.

Figure 48:
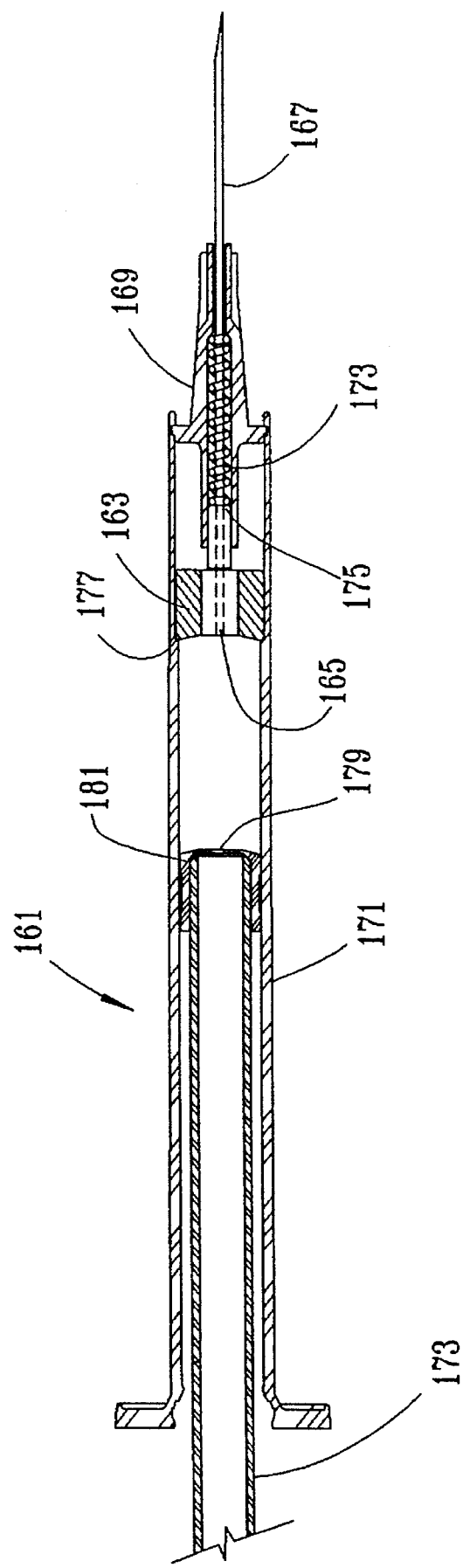
FIG. 48 of the drawings is a sectional view of a preferred embodiment of a syringe where no supports are utilized.

FIG. 48 of the drawings illustrates a preferred embodiment of a syringe 161 according to the present invention where no flexible or sacrificial supports are utilized. This embodiment is particularly suitable for small syringes, such as 1 cc, and includes a cylindrical deformable base 163 having a central passage therethrough which matingly engages a cylindrical enlarged needle head 165 which is attached to an end of hollow needle 167. A needle assembly 169 is attached to an end of barrel 171 opposite an end for insertion of plunger 173. Needle 167 passes through a passageway defined through needle assembly 169, and an energy storage means such as spring 173 is positioned within the passageway. Enlarged needle head 165 includes two cylindrical sections of different diameters with the larger section being held entirely within base 163 prior to initiation of needle retraction and the lower cylindrical section extending partially into the needle assembly and having a contacting portion 175 on an end thereof for contacting spring 173. Base 163 is biased in position by spring 173 against shelf 177 and by friction from barrel 171 prior to initiation of needle retraction.

Needle ejection through web 179 of boot 181 occurs as discussed with reference to syringe 1 above, which is incorporated herein, with base 163 being forced downwardly around the needle assembly except no supports are utilized. As base 163 moves downwardly, the enlarged needle head tears web 179, and when enlarged needle head 165 loses contact with base 163, needle 167 is ejected into plunger 7.

It is thus seen that this invention provides a novel syringe apparatus which minimizes the likelihood of accidental puncture, is operable by a single hand and which upon completion of injection captures the utilized needle and renders such harmless within the plunger and body of the syringe. As various other advantages and features will become apparent to those of skill in the art from a reading of the foregoing description which is exemplary in nature, such modifications and variations are embodied within the scope of this invention as defined by the following appended claims.

In the claims:

1. A syringe apparatus comprising:

a barrel;

a plunger movable within said barrel;

a needle assembly attached to an end of said barrel and defining a passageway therethrough;

a deformable base positioned within said barrel adjacent said needle assembly and defining a passage therethrough;

flexible supports included on said deformable base;

energy storage means within said passageway;

a hollow needle passing through said passageway;

an enlarged head on said needle engaged within said passage of said deformable base; and a rupturable web on an end of said plunger for moving a fluid within said barrel through the hollow of said needle when said plunger is moved through said barrel toward said needle assembly;

whereby when said plunger moves through said barrel toward said needle assembly, a fluid can be moved from said barrel through the hollow of said needle, and continued movement of said plunger flexes said supports and moves said deformable base downwardly until such time as sufficient force is imparted to said rupturable web by said enlarged head of said needle to tear said rupturable web, said deformable base then releasing said needle with said enlarged head due to force applied thereto by said energy storage means to project said needle with said enlarged head into the interior of said plunger.

2. The apparatus according to claim 1 wherein said enlarged head is generally matingly engaged by said deformable base.

3. The apparatus according to claim 1 wherein said plunger is hollow on the interior thereof for receipt of said needle and said enlarged head and further comprising means within said plunger for capturing said enlarged head of said needle when it is projected thereinto.

4. The apparatus according to claim 1 wherein said energy storage means is a spring.

5. The apparatus according to claim 1 wherein said flexible supports constitute an end of said deformable base and each includes an engaging flange on an end thereof.

6. The apparatus according to claim 5 wherein said deformable base is fitted against a shelf defined within said barrel at an end of said deformable base opposite said flexible supports.

7. The apparatus according to claim 1 wherein said flexible supports contact an end of said needle assembly.

8. The apparatus according to claim 1 wherein said rupturable web is part of a boot positioned over said end of said plunger.

9. The apparatus according to claims 1 or 3 wherein said rupturable web comprises at least one tear groove.

10. The apparatus according to claim 1 wherein said enlarged needle head comprises a flat and diametrically cylindrical top.

11. The apparatus according to claims 1 or 10 wherein said enlarged needle head is generally cylindrical and includes a plurality of areas diametrically wider than a remainder of said enlarged needle head.

12. The apparatus according to claim 1 wherein said needle assembly is attached to said barrel whereby said needle assembly partially extends into said barrel.

13. The apparatus according to claim 12 wherein said plunger has an enlarged operating head which is matingly receivable within an end of said barrel opposite said needle assembly.

14. The apparatus according to claim 1 further comprising a plunger seal for providing a liquid impervious seal between said plunger and said barrel at an end of said barrel opposite said needle assembly when said operating head of said plunger is received within said barrel.

15. The apparatus according to claim 14 wherein said plunger seal is an O-ring positioned within a groove on said plunger.

16. The apparatus according to claim 1 further comprising a needle guard positioned over said needle assembly.

17. The apparatus according to claim 16 further comprising a closing member for attachment to an end of said needle assembly to provide a liquid impervious seal therebetween, and wherein said closing member is removably attached to an end of said needle guard at an angle whereby said closing member can be attached to said needle assembly and removed from said needle guard without handling said closing member.

18. The apparatus according to claim 1 wherein said barrel has indicia thereon which is positioned above said deformable base when said deformable web is intact.

19. The apparatus according to claim 18 wherein said indicia and said deformable base are of substantially identical colors.

20. The apparatus according to claim 19 wherein said boot is a contrasting color to a color of said indicia.

21. The apparatus according to claim 1 further comprising means for revealing an indicia on said barrel.

22. A syringe apparatus comprising:

a barrel;

a hollow needle extending from an end of said barrel;

a plunger movable within said barrel for moving a fluid out of said barrel through said needle;

said plunger receivable within an end of said barrel opposite said needle; and a seal for providing a liquid impervious seal between said plunger and said barrel approximately at an end of said barrel opposite said needle.

23. The apparatus according to claim 22 wherein said seal is an O-ring positioned within a groove defined on said plunger.

24. A syringe apparatus comprising:

a barrel having an indicia thereon said indicia being covered by a shield;

a hollow needle extending from an end of said barrel;

a plunger movable within said barrel; and means for displacing said shield, thereby making said indicia readable upon movement of said plunger within said barrel.

25. The apparatus according to claim 24 wherein said barrel is generally transparent and said means for making said indicia readable comprises moving a component associated with said plunger of contrasting color to a color of said indicia below said indicia by movement of said plunger to make said indicia readable.

26. A syringe comprising:

a barrel having a first end and an opposite second end;

a plunger having a forward end and movable within said barrel from said second end of the barrel towards said first end, the plunger having a hollow interior communicating with said forward end;

a deformable base within said barrel intermediate said first and second end;

a hollow needle having a pointed front, said needle extending through said first end of said barrel and a rear end received within and supported by said deformable base;

energy storage means positioned in said barrel between said first end said deformable base and in engagement with said needle; and a rupturable web on said forward end of the plunger;

wherein a fluid can move from within said barrel through said needle as said plunger moves through said barrel to said deformable base, and when said rupturable web contacts said deformable base, continued movement of said plunger moves said deformable base toward said first end, said rear end of said needle thereby tearing said web wherein said rear end loses contact with said deformable base to allow said energy storage means to eject said needle into said interior of said plunger.

27. The apparatus according to claim 26 wherein said deformable base comprises flexible supports at an end thereof closest to said first end of said barrel.

28. The apparatus according to claim 27 further comprising a needle assembly attached to said first end of said barrel, said needle passing therethrough, and wherein said flexible supports are positioned against an end of said needle assembly opposite said pointed front prior to needle ejection.

29. The apparatus according to claim 28 wherein said deformable base and said needle assembly are of sizes so that said flexible supports can flex to surround said needle assembly and said needle assembly can pass within said deformable base as said deformable base moves toward said first end.

30. A process for retracting a needle upon completion of subcutaneous injection with a hypodermic syringe comprising the steps of:

forcing a plunger of a syringe downwardly within said syringe to force a deformable base engaging a head of said needle downwardly around said head;

forcing an end portion of said head to tear a base portion of said plunger; and propelling said needle into a hollow of said plunger.

31. The process according to claim 30 wherein said deformable base includes flexible supports and wherein said flexible supports are forced to flex away from one another prior to forcing said deformable base downwardly around said head.

32. The process according to claim 31 wherein said flexible supports are forced against a needle assembly through which said needle passes to force them to flex and wherein said supports flex just enough to pass around said needle assembly.

33. The process according to claim 30 further comprising capturing said needle within said hollow.

34. The process according to claim 30 further comprising sealing said plunger and said syringe to provide a liquid impervious seal to prevent any liquids therein from exiting.

35. The process according to claim 30 further comprising revealing a predetermined indicia on said syringe after said needle has been propelled into said hollow.

36. A process for plugging a passage left open by needle ejection in a syringe comprising the steps of:

providing a syringe having a passage with an opening left open by needle ejection;

providing a needle guard for covering said needle prior to needle ejection, said needle guard having a closing member for closing and sealing said passage opening attached thereto at an angle;

sealing off said passage opening by grasping said needle guard and attaching said closing member to said passage opening; and removing said needle guard from said closing member.

37. The process according to claim 36 wherein the step of sealing off said passage opening is accomplished wherein a user's hands and fingers remain behind said passage opening.

38. A syringe apparatus comprising:

a barrel;

a plunger movable within said barrel;

a needle assembly attached to an end of said barrel and defining a passageway therethrough;

a deformable base positioned within said barrel adjacent said needle assembly and defining a passage therethrough;

energy storage means within said passageway;

a hollow needle passing through said passageway;

an enlarged head on said needle engaged within said passage of said deformable base; and a rupturable web on an end of said plunger for moving a fluid within said barrel through the hollow of said needle when said plunger is moved through said barrel toward said needle assembly;

whereby when said plunger moves through said barrel toward said needle assembly, a fluid can be moved from said barrel through the hollow of said needle, and continued movement of said plunger moves said deformable base downwardly until such time as sufficient force is imparted to said rupturable web by said enlarged head of said needle to tear said rupturable web, said deformable base then releasing said needle with said enlarged head due to force applied thereto by said energy storage means to project said needle with said enlarged head into the interior of said plunger.

39. The apparatus according to claim 38 wherein said enlarged needle head is cylindrical.

40. The apparatus according to claim 38 wherein said deformable base is cylindrical.

* * * * *